US012642669B2

(12) United States Patent
Martin et al.

(10) Patent No.: US 12,642,669 B2
(45) Date of Patent: Jun. 2, 2026

(54) SECUREMENT PLATE FOR INTERVERTEBRAL IMPLANT

(71) Applicant: Medos International Sarl, Le Locle (CH)

(72) Inventors: Thomas Martin, Riverside, RI (US); Kurt Schmura, Middleboro, MA (US); Cory Emil, Milton, MA (US); Derek Redder, Warren, RI (US)

(73) Assignee: Medos International Sarl, Le Locle (CH)

( * ) Notice: Subject to any disclaimer, the term of this patent is extended or adjusted under 35 U.S.C. 154(b) by 159 days.

(21) Appl. No.: 18/320,296

(22) Filed: May 19, 2023

(65) Prior Publication Data

US 2023/0372122 A1     Nov. 23, 2023

Related U.S. Application Data

(60) Provisional application No. 63/343,992, filed on May 19, 2022.

(51) Int. Cl.
*A61F 2/46*        (2006.01)
*A61F 2/30*        (2006.01)
*A61F 2/44*        (2006.01)

(52) U.S. Cl.
CPC ........ *A61F 2/4611* (2013.01); *A61F 2/30771* (2013.01); *A61F 2/44* (2013.01); *A61F 2002/30579* (2013.01)

(58) Field of Classification Search
CPC .......... A61F 2/30; A61F 2/30771; A61F 2/44; A61F 2/4455; A61F 2/46; A61F 2/4611; A61B 17/17; A61B 17/1757
See application file for complete search history.

(56) References Cited

U.S. PATENT DOCUMENTS

| | | | |
|---|---|---|---|
| 6,066,175 | A | 5/2000 | Henderson et al. |
| 6,228,085 | B1 | 5/2001 | Theken et al. |
| 6,428,542 | B1 | 8/2002 | Michelson |
| 6,565,571 | B1 | 5/2003 | Jackowski et al. |
| 7,288,095 | B2 | 10/2007 | Baynham et al. |
| 7,303,564 | B2 | 12/2007 | Freid et al. |
| 7,625,378 | B2 | 12/2009 | Foley |

(Continued)

FOREIGN PATENT DOCUMENTS

| | | |
|---|---|---|
| EP | 2175789 A1 | 4/2010 |
| WO | 2013/134210 A1 | 9/2013 |

(Continued)

*Primary Examiner* — Christopher J Beccia
(74) *Attorney, Agent, or Firm* — Flaster Greenberg P.C.

(57) ABSTRACT

Plates are described for securement to an intervertebral implant, and for fixation to a vertebral body so as to stabilize the implant during the surgical procedure, and in particular as the patient is repositioned during the surgical procedure, for instance from from a lateral decubitus position to a prone position. The plate includes a securement member that is movable between an unlocked configuration whereby the securement member is positioned for insertion into the implant, and a locked configuration that couples the securement member to the intervertebral implant. The securement member is further movable to a secured position that secures the plate to the intervertebral implant as to to define a rigid construct.

19 Claims, 19 Drawing Sheets

(56) References Cited

U.S. PATENT DOCUMENTS

| | | | |
|---|---|---|---|
| 7,662,174 | B2 | 2/2010 | Doubler et al. |
| 7,875,062 | B2 | 1/2011 | Lindemann et al. |
| 8,062,294 | B2 | 11/2011 | Reynolds |
| 8,097,027 | B2 | 1/2012 | Lim et al. |
| 8,109,934 | B2 | 2/2012 | Guenther et al. |
| 8,114,138 | B2 | 2/2012 | Nehls |
| 8,118,847 | B2 | 2/2012 | Wallenstein et al. |
| 8,172,885 | B2 | 5/2012 | Songer et al. |
| 8,216,284 | B2 | 7/2012 | Leung |
| 8,216,312 | B2 | 7/2012 | Gray |
| 8,328,856 | B1 | 12/2012 | Donahoe et al. |
| 8,425,573 | B2 | 4/2013 | Erickson et al. |
| 8,480,716 | B2 | 7/2013 | Perrow et al. |
| 8,500,811 | B2 | 8/2013 | Blain et al. |
| 8,556,944 | B2 | 10/2013 | Dube et al. |
| 8,574,271 | B2 | 11/2013 | Crainich |
| 8,709,014 | B2 | 4/2014 | Ammann |
| 8,828,084 | B2 * | 9/2014 | Aflatoon ............... A61F 2/4465 |
| | | | 623/17.16 |
| 8,986,354 | B2 | 3/2015 | Walker |
| 8,998,988 | B2 | 4/2015 | Phillips et al. |
| 9,044,344 | B2 | 6/2015 | Nelson et al. |
| 9,101,422 | B2 | 8/2015 | Freid et al. |
| 9,241,749 | B2 | 1/2016 | Lombardo et al. |
| 9,301,785 | B2 | 4/2016 | Wallenstein |
| 9,326,861 | B2 | 5/2016 | Ott et al. |
| 9,364,272 | B2 | 6/2016 | Binder et al. |
| 9,486,263 | B2 | 11/2016 | Kirschman |
| 9,603,611 | B2 | 3/2017 | Perry |
| 9,642,652 | B2 | 5/2017 | Scioscia et al. |
| 9,662,145 | B2 | 5/2017 | Harris et al. |
| 9,730,804 | B2 | 8/2017 | Cowan, Jr. et al. |
| 9,763,715 | B2 | 9/2017 | Mather et al. |
| 9,848,925 | B2 | 12/2017 | Ziolo et al. |
| 10,010,357 | B2 | 7/2018 | Ziolo et al. |
| 10,064,666 | B2 | 9/2018 | Dunaway |
| 10,076,369 | B2 | 9/2018 | Chin et al. |
| 10,143,499 | B2 | 12/2018 | Milz et al. |
| 10,159,514 | B2 | 12/2018 | Perrow et al. |
| 10,159,517 | B2 | 12/2018 | Leduc et al. |
| 10,206,720 | B2 | 2/2019 | Laubert et al. |
| 10,213,318 | B2 | 2/2019 | Refai |
| 10,231,763 | B2 | 3/2019 | Black et al. |
| 10,238,439 | B2 | 3/2019 | Prybis et al. |
| 10,265,109 | B2 | 4/2019 | Lauf et al. |
| 10,420,653 | B2 | 9/2019 | Liu et al. |
| 10,433,978 | B2 | 10/2019 | Bullard |
| 10,463,504 | B2 | 11/2019 | Vestgaarden |
| 10,543,030 | B2 | 1/2020 | Seavey et al. |
| 10,543,104 | B2 | 1/2020 | Petersheim et al. |
| 10,561,450 | B2 | 2/2020 | Thiel et al. |
| 10,568,664 | B2 | 2/2020 | Blain et al. |
| 10,603,187 | B2 * | 3/2020 | Laubert .................. A61F 2/447 |
| 10,667,828 | B2 | 6/2020 | Biedermann |
| 10,716,687 | B2 | 7/2020 | Nino et al. |
| 10,751,191 | B1 | 8/2020 | Tumialan |
| 10,799,276 | B2 | 10/2020 | Dacosta et al. |
| 10,828,075 | B2 | 11/2020 | Gault |
| 10,828,174 | B2 | 11/2020 | Melkent et al. |
| 10,849,763 | B2 | 12/2020 | Lauf et al. |
| 10,912,591 | B2 | 2/2021 | Altarac et al. |
| 2004/0153091 | A1 | 8/2004 | Figueroa et al. |
| 2007/0225718 | A1 | 9/2007 | Ensign |
| 2008/0234689 | A1 | 9/2008 | Melkent et al. |
| 2008/0294262 | A1 | 11/2008 | Levieux |
| 2009/0192549 | A1 | 7/2009 | Sanders et al. |
| 2009/0270926 | A1 | 10/2009 | Hawkes |
| 2011/0238123 | A1 | 9/2011 | Kirschman |
| 2015/0119943 | A1 | 4/2015 | Milella et al. |
| 2015/0245859 | A1 | 9/2015 | Mcmillen et al. |
| 2017/0065311 | A1 | 3/2017 | George et al. |
| 2019/0008659 | A1 * | 1/2019 | Melkent ............... A61F 2/4455 |
| 2019/0090925 | A1 | 3/2019 | Detweiler et al. |
| 2019/0175236 | A1 | 6/2019 | Blacklidge et al. |
| 2019/0247203 | A1 | 8/2019 | Nino |
| 2020/0000501 | A1 | 1/2020 | Gephart |
| 2020/0281736 | A1 | 9/2020 | Milz et al. |
| 2020/0352613 | A1 | 11/2020 | Agarwal et al. |
| 2021/0059726 | A1 | 3/2021 | Artaki et al. |
| 2021/0085482 | A1 | 3/2021 | Flickinger et al. |

FOREIGN PATENT DOCUMENTS

| | | | |
|---|---|---|---|
| WO | 2018/208070 | A1 | 11/2018 |
| WO | 2021/016022 | A1 | 1/2021 |
| WO | 2021/030645 | A1 | 2/2021 |

* cited by examiner

SECUREMENT PLATE FOR INTERVERTEBRAL IMPLANT

CROSS-REFERENCE TO RELATED APPLICATIONS

This application claims priority to U.S. Patent Application Ser. No. 63/343,992 filed May 19, 2022, the disclosure of which is hereby incorporated by reference as if set forth in its entirety herein.

BACKGROUND

The human spine is comprised of a series of vertebral bodies separated by intervertebral discs. The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1.beta. and TNF-.alpha. as well as matrix metalloproteinases ("MMPs"). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc from the intervertebral disc space, and replace it with an intervertebral implant that restores disc height and allows for bone fusion with the adjacent vertebrae. These devices are commonly called fusion devices, or "interbody fusion devices". Current spinal fusion procedures include transforaminal lumbar interbody fusion (TLIF), posterior lumbar interbody fusion (PLIF), and extreme lateral interbody fusion (XLIF) procedures. Once the fusion device has been inserted into the intervertebral disc space, the patient is often repositioned from a lateral decubitus position to a prone position in order to implant supplemental fixation.

What is therefore needed is a method and apparatus for maintaining the position of the fusion device in the intervertebral disc space during patient repositioning.

SUMMARY

In one example, a plate is configured to secure to an intervertebral implant that extends in a distal direction from the plate. The plate can include a plate body having at least one bone fixation hole configured to receive a bone fixation element that extends into a vertebral body, wherein the plate body defines a seat. The plate can further include a securement member configured to rotate in a first direction of rotation about an axis of rotation from an unlocked configuration to a locked configuration. In one example, the securement member can be configured to be driven to translate in a securement direction along the axis of rotation to a secured position until a retention wall of the intervertebral implant is captured between the seat and the securement member when the securement member is in the locked configuration.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the intervertebral implant of the present application, there is shown in the drawings illustrative embodiments. It should be understood, however, that the application is not limited to the precise arrangements and instrumentalities shown. In the drawings.

DETAILED DESCRIPTION

Figures 11A, 11B:
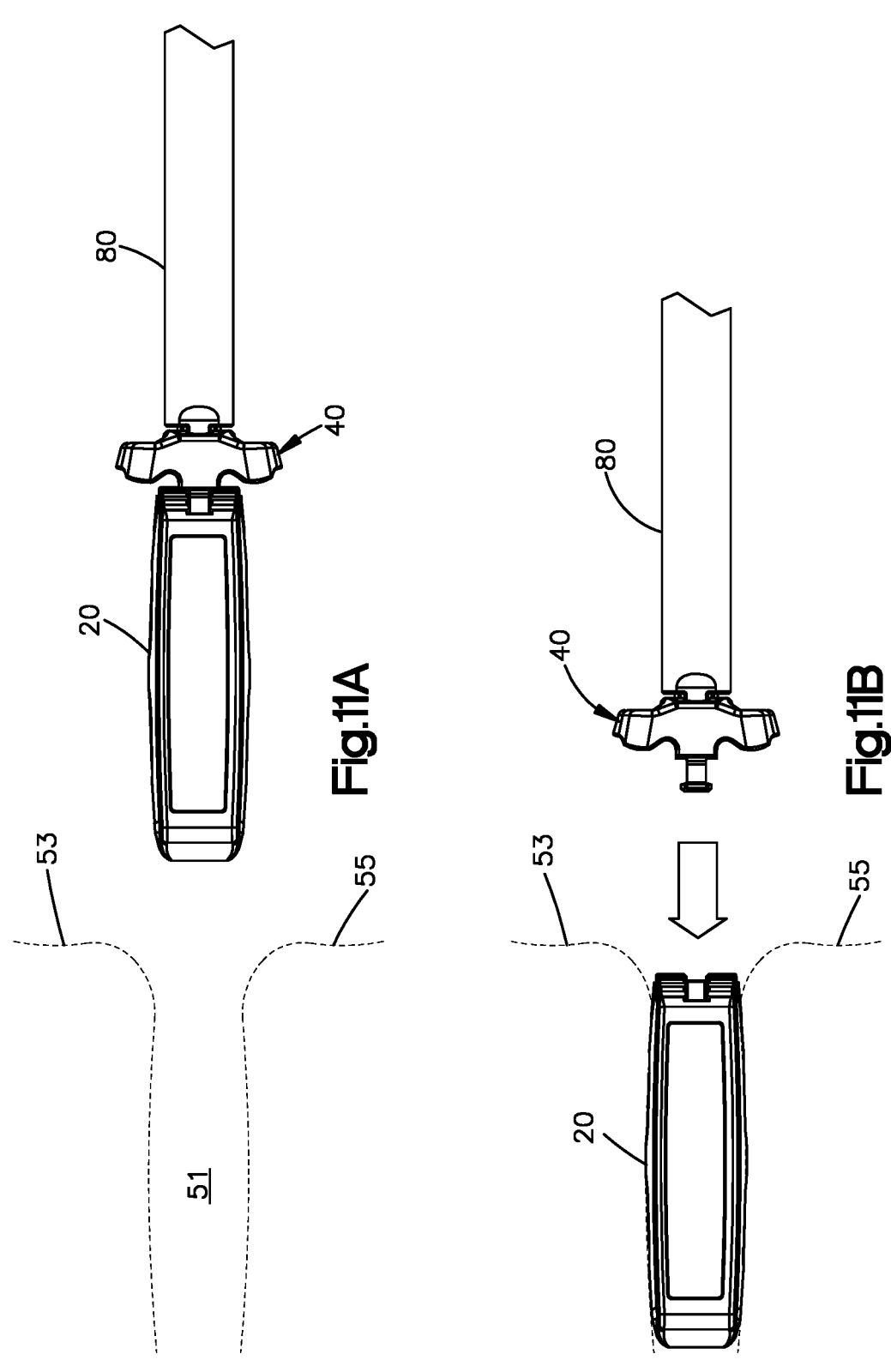
FIG. 11A is a side elevation view of the driver and inserter coupled to the plate, and showing the plate secured to the implant prior to inserting the implant into an intervertebral space.
FIG. 11B is a side elevation view of the driver and inserter coupled to the plate, and configured to couple the plate to the implant after the implant has been inserted into the intervertebral space.

Referring initially to FIGS. 1A-1E, an intervertebral implant 20 is configured to be inserted into an intervertebral space. As shown at FIGS. 11A-11B, the intervertebral space 51 can be defined by a superior vertebral body 53 and an adjacent inferior vertebral body 55 of a human spine. The superior vertebral body 53 defines a superior vertebral surface. The inferior vertebral body 55 defines an inferior vertebral surface. The inferior and superior vertebral surfaces can cooperate to define the intervertebral space 51. The vertebral bodies 53 and 55 can be anatomically adjacent each other. It should be understood, however, that the intervertebral implant 20 can alternatively be configured to fit in an intervertebral space that is defined by superior and inferior vertebral bodies that remain after a corpectomy has been performed so as to remove one or more vertebral bodies between the superior and inferior vertebral bodies. The intervertebral implant can be inserted into the intervertebral space after a discectomy has been performed, whereby the intervertebral disc material has been removed or at least partially removed to prepare the intervertebral space to receive the intervertebral implant. The intervertebral space can be defined in the lumbar region of the spine, or alternatively in the cervical region or the thoracic region of the spine.

As will be appreciated from the description below, the intervertebral implant 20 is configured to be inserted into the intervertebral space along a lateral anatomical approach (referred to as a lateral intervertebral implant). It is appreciated, however, that the present invention is not limited to a lateral intervertebral implant unless otherwise indicated, and can for instance be a TLIF implant, a PLIF implant, or an XLIF implant.

Referring now to FIGS. 1A-1E, the intervertebral implant 20 is described herein as extending horizontally along a longitudinal direction "L" and a lateral direction "A", and transversely along a transverse direction "T". Unless otherwise specified herein, the terms "longitudinal," "lateral," and "transverse" are used to describe the orthogonal directional components of various implant components and implant component axes. The longitudinal direction L can be perpendicular to the transverse direction T. The lateral direction A can be perpendicular to the longitudinal direction L and the transverse direction T. It should be appreciated that while the longitudinal and lateral directions are illustrated as extending along horizontal directions, and that the transverse direction T is illustrated as extending along a vertical direction, the directions may differ during use depending on the orientation of the implant. For instance, when the implant 20 is inserted into an intervertebral space, the transverse direction T extends generally along the superior-inferior (or caudal-cranial) direction, while the horizontal plane defined by the longitudinal direction L and lateral direction A lies generally in the anatomical plane defined by the anterior-posterior direction, and the medial-lateral direction. For instance, the lateral direction A can extend generally along the anterior-posterior direction. The longitudinal direction L can extend generally along the medial-lateral direction.

The intervertebral implant 20 defines a leading end 22 and a trailing end 24 opposite the leading end 22 along a longitudinal direction L. The longitudinal direction L can generally extend along an insertion direction into the intervertebral space. Thus, the longitudinal direction L can be said to extend along the anatomical medial-lateral direction after the intervertebral implant 20 has been inserted into the intervertebral space along the insertion direction. In particular, the leading end 22 can be said to be spaced from the trailing end 24 in the insertion direction. The leading end 22 can be tapered so as to facilitate insertion into the intervertebral space. The trailing end 24 is spaced from the leading end 22 in a direction that is opposite the insertion direction. The leading end 22 can also be said to define a distal end, and the trailing end 24 can be said to define a proximal end that is opposite the distal end. Thus, the implant 20 can be said to define a distal direction from the trailing end 24 to the leading end 22 along the longitudinal direction L. The implant 20 can also be said to define a proximal direction from the leading end 22 to the trailing end 24 along the longitudinal direction L. Thus, the distal direction can be coincident with the insertion direction. The proximal direction can be coincident with the direction opposite the insertion direction.

The intervertebral implant 20 can further define first and second opposed side surfaces 26 and 28 that are opposite each other along a lateral direction A. When the intervertebral implant 20 is a lateral implant, the first side surface 26 can define an anterior side surface, and the second side surface 28 can define a posterior side surface. The lateral direction A can be oriented perpendicular to each of the longitudinal direction L and the transverse direction T. The lateral direction A can be said to define a width of the implant. When the intervertebral implant 20 is a lateral implant, the width can be measured along the anatomical anterior-posterior direction.

The intervertebral implant 20 can define an upper surface 30 that is configured to engage and contact the superior vertebral surface of the superior vertebra, and a lower surface 32 that is configured to engage and contact the inferior vertebral surface of the inferior vertebra. Thus, the upper surface 30 can be referred to as an upper or superior vertebral bone contacting surface, and the lower surface 32 can be referred to as a lower or inferior vertebral bone contacting surface. The upper and lower surfaces 30 and 32 are spaced from each other along the transverse direction T that is oriented perpendicular to each of the longitudinal direction L and the lateral direction A. The transverse direction T can define a height of the intervertebral implant 20. The height can be measured along the anatomical caudal-cranial direction. The height of the intervertebral implant 20 can be measured along the transverse direction T from the upper surface 30 to the lower surface 32. As used herein, the term "superior" and derivatives thereof refer to a direction from the lower surface 32 toward the upper surface 30. As used herein, the term "inferior" and derivatives thereof refer to a direction from the upper surface 30 toward the lower surface 32.

In one example, the intervertebral implant 20 can be configured to define a lordotic or kyphotic profile as desired. Thus, the anterior side surface 26 can define a height along the transverse direction T that is equal to the height of the posterior side surface 28 along the transverse direction T. Alternatively, the anterior side surface 26 can define a height along the transverse direction T that is greater than the height of the posterior side surface 28 along the transverse direction T. For instance, one or both of the upper and lower surfaces 30 and 32 can be sloped with respect to each other in a direction from the anterior side surface 26 to the posterior side surface 28. The slope of either or both of the upper surface 30 and the lower surface 32 can be defined in a plane that is oriented along the transverse direction T and the lateral direction A. In one example, the lower surface 32 can be sloped, and the upper surface 30 can be oriented substantially along a plane that is defined by the longitudinal direction L and the lateral direction A. Alternatively, the upper surface 30 can be sloped, and the lower surface 32 can be oriented substantially along a plane that is defined by the longitudinal direction L and the lateral direction A. Alternatively still, each of the upper and lower surfaces 30 and 32 can be sloped. The upper and lower surfaces 30 and 32 can define any suitable angle as desired in the plane that is defined by the lateral direction A and the transverse direction T. The angle can be substantially 8 degrees, substantially 16 degrees, or any other angle as desired. Alternatively, the upper surface 30 and the lower surface 32 can be substantially parallel to each other as desired. The implant 20 can be 3D printed or otherwise constructed as desired. Further, the implant 20 can be non-expandable or expandable along the transverse direction T as desired.

With continuing reference to FIGS. 1A-1E, a bone fixation system 38 can include the intervertebral implant 20 and a plate 40 that is configured to be secured to the implant 20 and is further configured to be coupled to at least one or both of the vertebrae that define the intervertebral disc space. The implant 20 can extend in a distal direction from the plate 40 into the intervertebral disc space. Advantageously, the plate 40 can stabilize the implant 20 to limit or prevent migration of the implant 20 as the patient is repositioned during the surgical procedure. For instance, the plate 40 can be secured to the implant 20 and coupled to the at least one of the vertebrae while the patient is in the lateral decubitus position. Therefore, when the patient is repositioned to a prone position the plate 40 limits or prevents migration of the implant 20 in the intervertebral space.

The plate 40 can include a plate body 41 that defines a front surface 42 that faces the intervertebral implant 20 and the vertebrae, and a rear surface 44 opposite the front surface 42. The front surface 42 can be said to be spaced from the rear surface 44 in a forward direction, which can also be the insertion direction of the intervertebral implant 20. Thus, the forward direction can define the distal direction. Conversely the rear surface 44 can be said to be spaced from the front surface 42 in a rearward direction that is opposite the forward direction. Thus, the rearward direction can be referred to as a proximal direction.

The plate 40 can include at least one bone fixation hole 46 that extends through the plate body 41 from the front surface 42 to the rear surface 44. When the plate 40 is secured to the intervertebral implant 20 when the intervertebral implant 20 is implanted, the bone fixation hole 46 can be receive a bone fixation element 48 that is inserted through the hole 46 and into one of the intervertebral bodies. In one example, the plate 40 can include two fixation holes, defined by first and second fixation holes 46a and 46b, that are positioned such that a first bone fixation element 48a can be driven through the first fixation hole 46a and into the superior vertebra. A second bone fixation element 48b can be driven through the second fixation hole 46b and into the inferior vertebra. In one example, the bone fixation element can be configured as a bone screw. Thus, the first fixation hole 46a can be referred to as a superior fixation hole, and the second fixation hole 46b can be referred to as an inferior fixation hole. Thus, the plate 40 can have two and no more than two fixation holes in one example. As will be appreciated from the description below, in other examples the plate 40 can include only a single bone fixation hole.

As will now be described, the plate 40 is configured to be secured to the intervertebral implant 20. In particular, referring now to FIGS. 2A-2C, the plate 40 can include a securement member 50 supported by the plate body 41. The securement member 50 is rotatable with respect to the plate body 41 about an axis of rotation 43, and is also translatable with respect to the plate body 41 along the axis of rotation 43. The axis of rotation 43 can be defined by the longitudinal direction L, and can be defined by a central axis of the securement shaft. The securement member 50 can include a securement shaft 52 that is supported in the plate body 41, and an enlarged securement head 54 that extends out from the securement shaft 52 along a direction perpendicular to the longitudinal direction L. The securement head 54 can be oblong and is in a first orientation in the unlocked configuration, and a second orientation different than the first orientation in the locked configuration. For instance, the securement head 43 can extend in opposite directions from the securement shaft, and in particular from a terminal distal end of the securement shaft 52. Thus, the securement member 50 can be substantially T-shaped. The securement head 54 can be disposed distal of the plate body 41 when the securement shaft 52 is supported by the plate body 41. A distal portion of the securement shaft 52 can extend out from the plate body 41 and can terminate at the securement head 54.

Figures 1A, 1B:
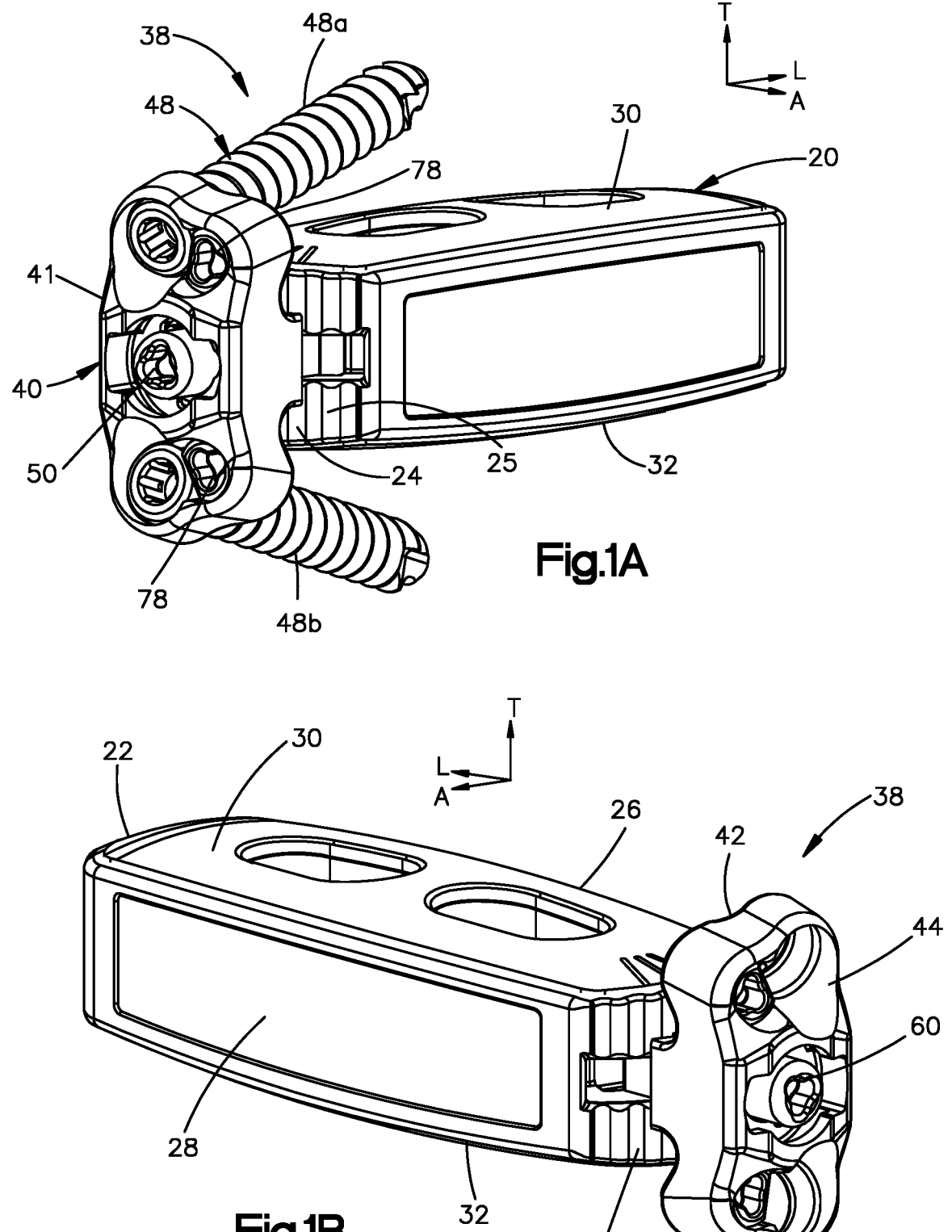
FIG. 1A is a perspective view of a bone fixation system including an intervertebral implant and a plate secured to the intervertebral implant, showing screws inserted through screw holes of the plate.
FIG. 1B is another perspective view of the bone fixation system of FIG. 1A, wherein the screws are omitted.
Figures 1C, 1D, 1E:
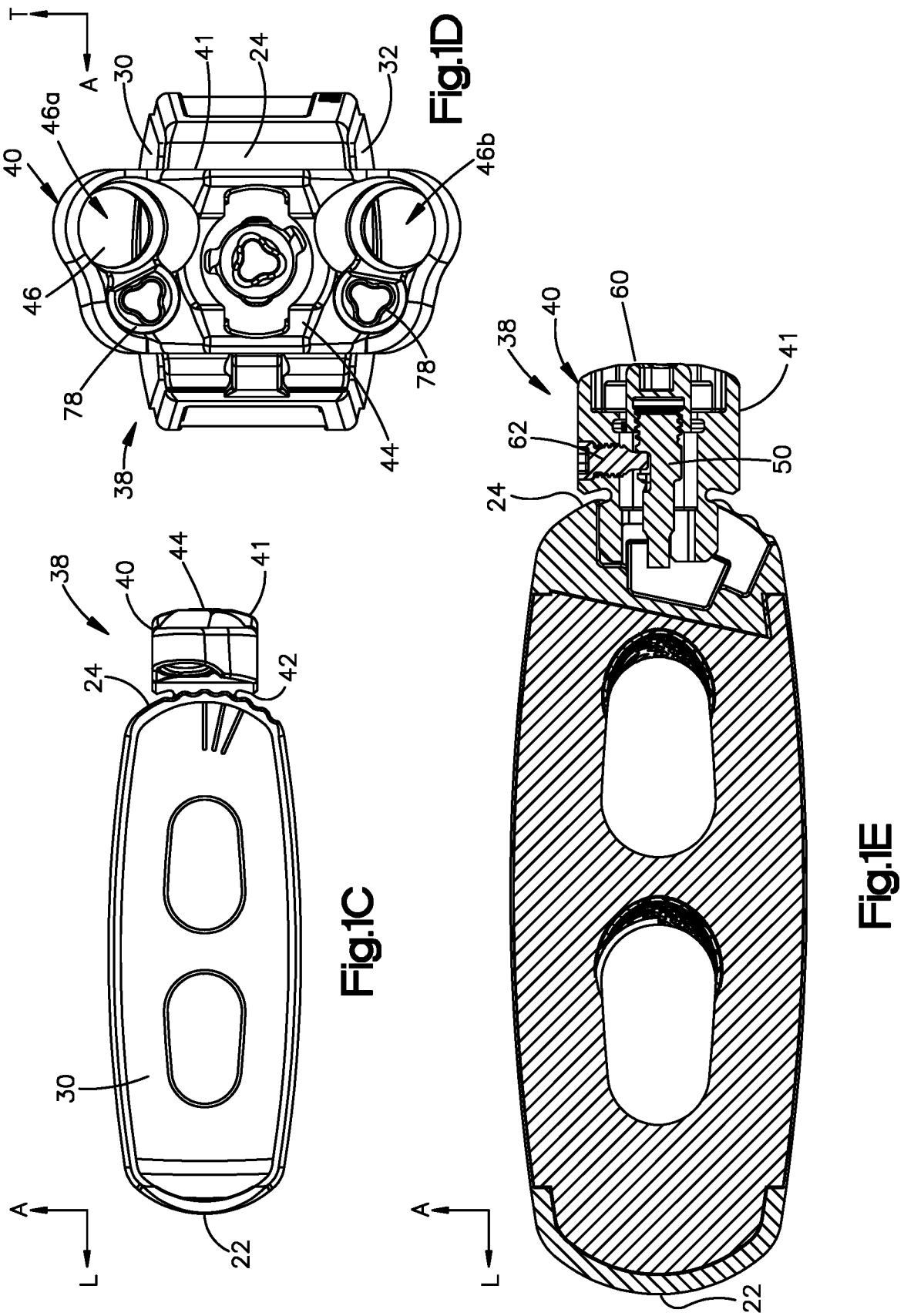
FIG. 1C is a top plan view of the bone fixation system of FIG. 1B.
FIG. 1D is a side elevation view of the bone fixation system of FIG. 1C.
FIG. 1E is a cross-sectional view of the bone fixation system of FIG. 1D.
Figure 2A:
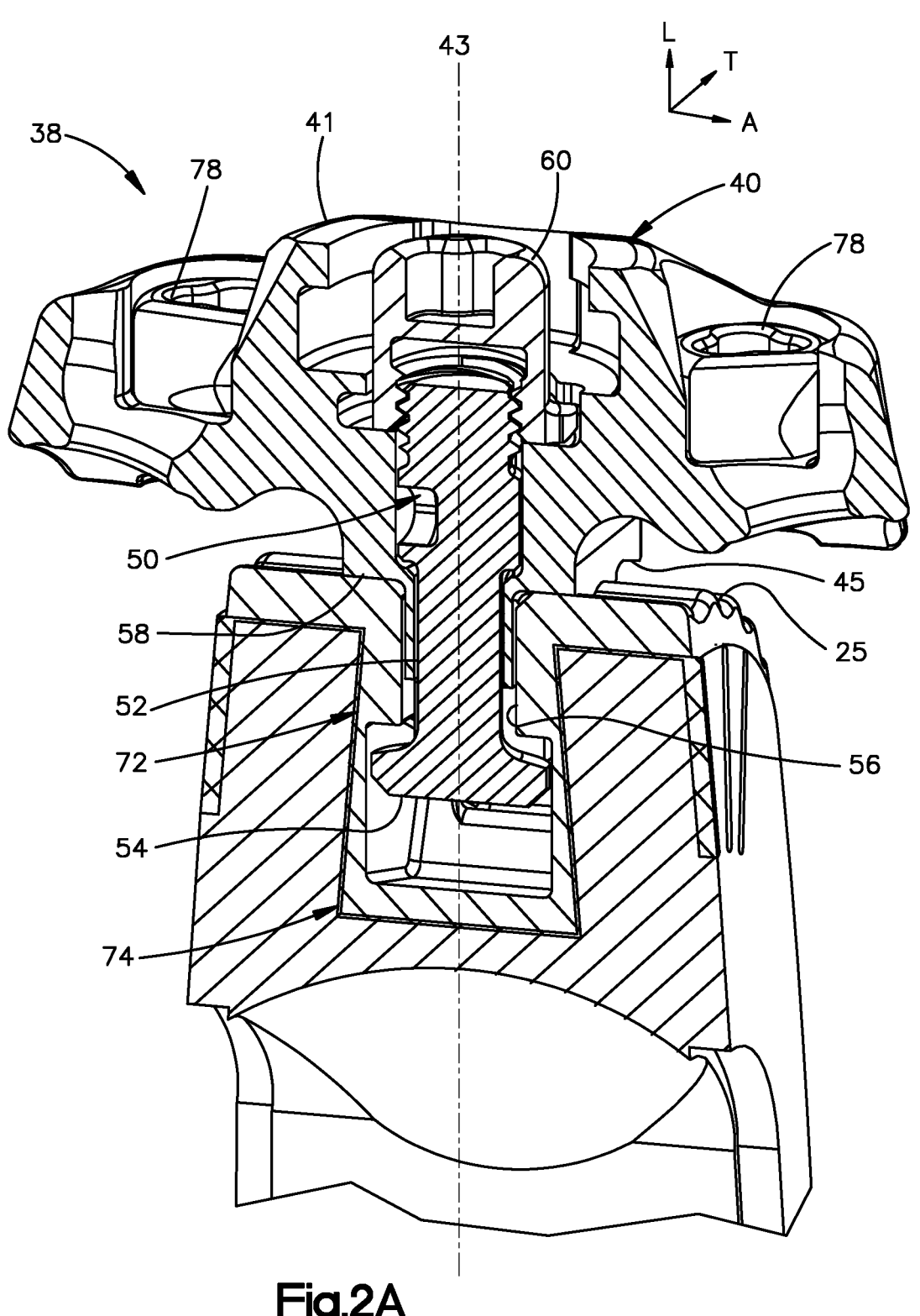
FIG. 2A is a cross-sectional view of the bone fixation system of FIGS. 1A-1E constructed in accordance with one example and shown in a locked configuration.

The securement member 50 is configured to rotate in a first direction of rotation about an axis of rotation 43 from an unlocked configuration to a locked configuration. The securement head 54 can be a first orientation in the unlocked configuration (FIGS. 2B-2C), and a second orientation different than the first orientation in the locked configuration (FIG. 2A). In particular, the securement member 50 can further rotate in a second direction of rotation opposite the first direction of rotation from the locked configuration to the unlocked configuration. In the unlocked configuration, the securement member 50 can be removed from the intervertebral implant 20 by translating the plate 40 proximally away from the implant 20. When the securement member is in the locked configuration, the securement member 50 and in particular the securement head 54 is longitudinally aligned with a retention wall 56 of the implant 20 along the longitudinal direction L, as shown in FIG. 2A. Further, the securement head 54 is positioned distal of the retention wall 56. Therefore, movement of the plate 40 in the proximal direction with respect to the implant 20 will cause the securement head 54 to abut the retention wall 56, thereby preventing removal of the plate 40 from the implant 20. When securement member 50 is in the unlocked configuration shown in FIGS. 2B-2C, the securement head 54 is out of alignment with the retention wall along the longitudinal direction L. The first and second orientations of the securement head 54 can be angularly offset from each other by any amount as desired, such as by approximately 90 degrees.

When the securement member 50 is in the locked configuration, the securement member 50 is configured to be driven to translate in a securement direction along the axis of rotation 43 such that the securement head 54 travels toward a seat 58 of the plate 40, and in particular of the plate body 41. The securement direction can be defined by the proximal direction in some examples. The seat 58 can be defined by the front surface 42 of the plate body 41. The securement member 50 travels in the securement direction until the securement member 50 reaches a secured position whereby the retention wall 56 is captured between the seat 58 and the securement member 50. In particular, the securement member 50 is configured to translate in the securement direction until the retention wall 56 is captured between the seat 58 and the securement head 54. When the retention wall 56 is captured, the plate 40 and the implant 20 can define a rigid construct.

Figure 2B:
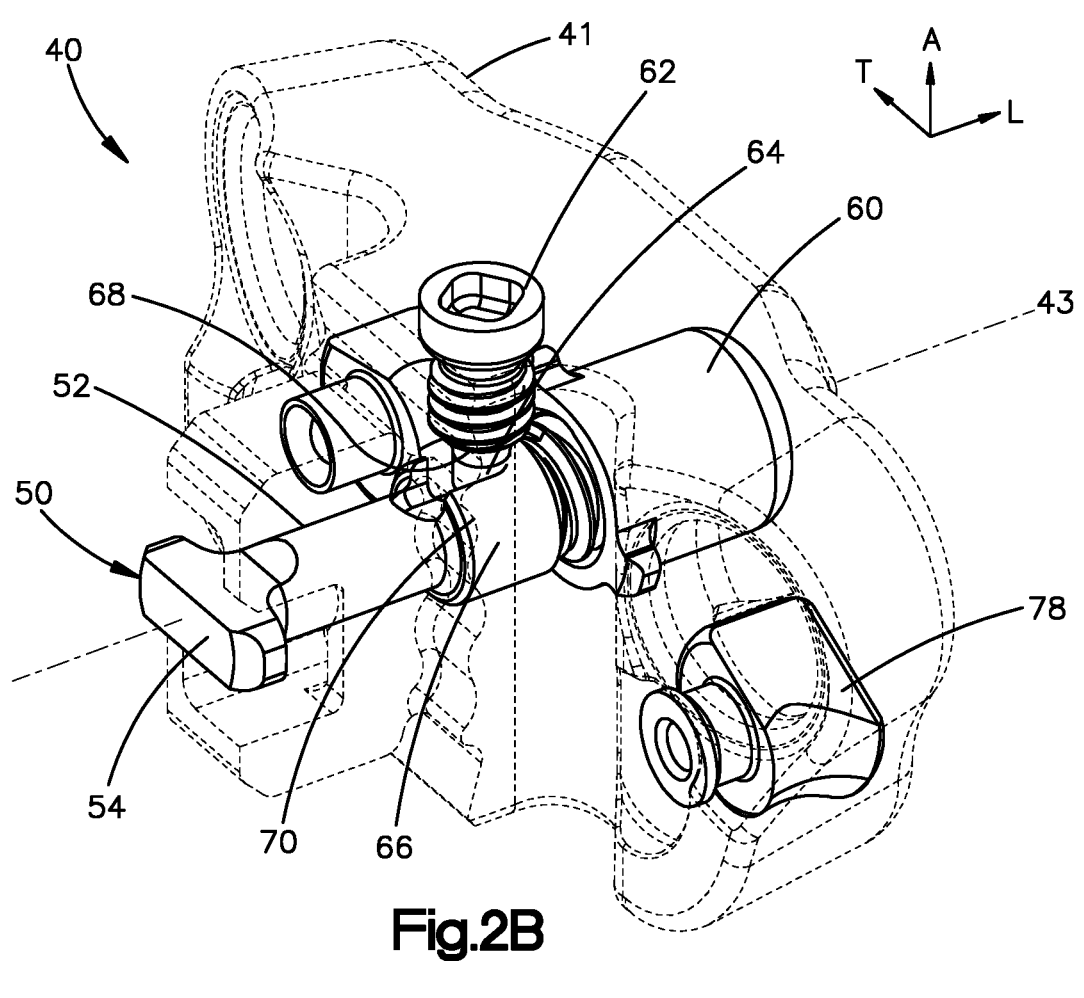
FIG. 2B is a perspective view of the plate of the bone fixation system of FIG. 2A shown in an unlocked configuration, whereby portions of the plate are shown transparent.
Figure 2C:
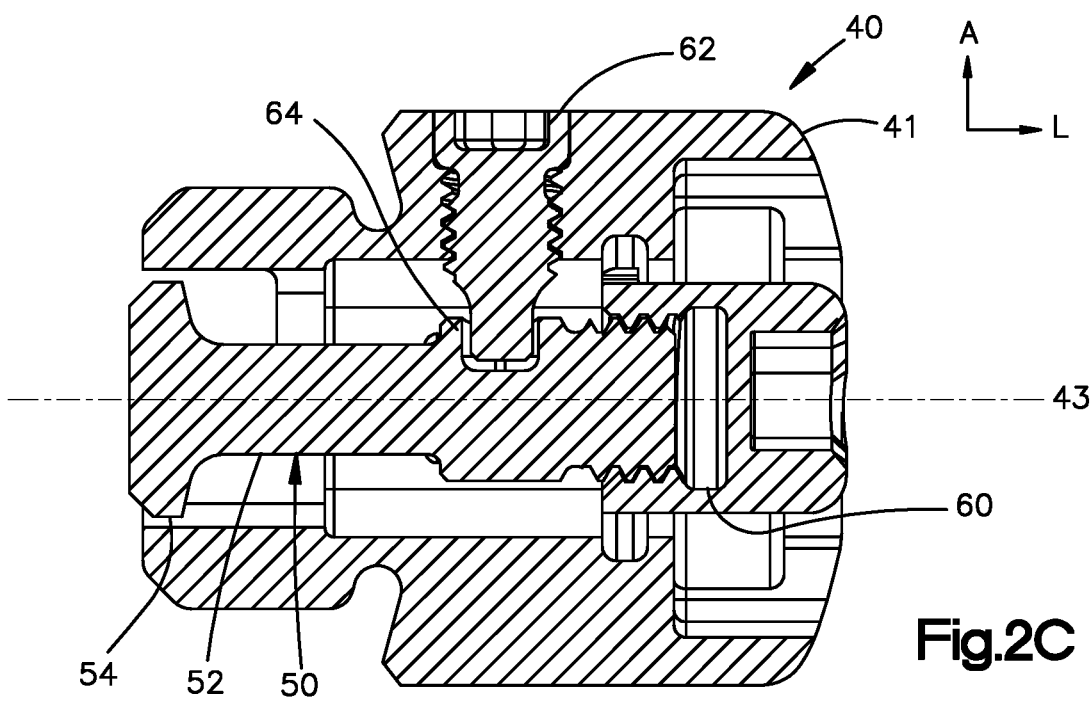
FIG. 2C is a sectional elevation view of the plate of FIG. 2B.

With continuing reference to FIGS. 2A-2C, the plate 40 can further include an actuator 60 that is threadedly mated with the securement shaft 52. In this regard, a proximal end portion of the securement shaft 52 can be threaded. The actuator 60 can define a cap that is disposed over the proximal end portion of the securement shaft 52 and threaded to the proximal end portion of the securement shaft 52. The actuator 60 can be configured to rotate in the first direction of rotation during a first stroke of rotation to drive the securement member 50 to rotate in the first direction of rotation to the locked configuration. Thus, during the first stroke of rotation of the actuator 60, the actuator 60 and the securement member 50 are rotatably coupled. The actuator 60 can then be further rotated in the first direction of rotation during a second stroke of rotation during which the actuator 60 rotates relative to the securement shaft 52. Thus, the actuator 60 and the securement shaft 52 are rotatably decoupled during the second stroke of rotation. It should be recognized that the second stroke of rotation can be continuous with the first stroke of rotation. Because the actuator 60 is threadedly coupled to the securement shaft 52, rotation of the actuator during the second stroke of rotation causes the securement shaft 52 to translate or otherwise travel in the securement direction with respect to the plate body 41 and the implant 20.

The plate 40 can further include an auxiliary shaft 62 that can provide a locking member positionally fixed to the plate body 41 and configured to interface with the securement shaft 52 during rotation and translation of the securement shaft 52. In particular the auxiliary shaft 62 can extend into a slot 64 of the securement member 50 and in particular of the securement shaft 52. The slot 64 can extend circumferentially about the axis of rotation 43 along a portion of the outer periphery of the securement shaft 52. The slot 64 can be defined by first and second ends that define first and second stop surfaces 66 and 68, respectively, that the auxiliary shaft 62 can abut during use. For instance, when the securement shaft 52 is in the unlocked configuration, the auxiliary shaft 62 can abut the second stop surface 68.

During the first stoke of rotation of the actuator 60, the actuator 60 and the securement member 50 rotate relative to the plate together until the first stop surface 66 is brought against the auxiliary shaft 62. As the actuator 60 rotates during the first stroke of rotation, the securement member 50 similarly rotates from the unlocked configuration to the locked configuration. The abutment between the auxiliary shaft 62 and the first stop surface prevents the securement member 50 from continuing to rotate in the first direction relative to the plate 40. Therefore, continued rotation of the actuator 60 in the first direction of rotation is relative to the securement member 50. The threaded connection between the actuator 60 and the securement member 50 causes the securement member 50 to move in the securement direction during the second stroke of rotation of the actuator 60. The slot 64 of the securement member 50 can define a longitudinal opening 70 adjacent the first stop surface 66. The longitudinal opening 70 can extend distally, such that the auxiliary shaft 62 travels into the longitudinal opening as the securement member travels proximally in the securement direction relative to the plate body 41 and the auxiliary shaft 62. It should be appreciated in one example that the actuator 60 drives the securement member 50 to travel in the securement direction only when the securement member 50 is in the locked configuration.

If it is desirable to decouple the plate 40 from the implant 20, the actuator 60 can be rotated relative to the plate body 41 in a second direction of rotation opposite the first direction of rotation. Rotation of the actuator 60 in the second direction of rotation causes the auxiliary shaft 62 to abut a surface of the securement member 50, and in particular of the securement shaft 52, that partially defines the longitudinal opening 70. Thus, the securement member 50 is unable to rotate in the second direction of rotation relative to the plate body 41, and the actuator 60 thus rotates relative to the securement member 50. The relative rotation of the actuator 60 in the second direction of rotation relative to the securement member 50 causes the securement member 50 to travel distally in a disengagement direction whereby the securement head 54 travels away from the retention wall 56 of the implant 20 and the seat 58 of the plate body 41. The securement member 50 continues to travel distally until the auxiliary shaft 62 is disposed in the slot 64, which then rotatably couples the securement member 50 and the actuator 60 in the second direction of rotation. The actuator 60 rotates with the securement member 50 in the second direction of rotation to the unlocked configuration whereby the auxiliary shaft 62 seats against the second stop member 68, which prevents further rotation of the actuator 60 and the securement member 50 in the second direction of rotation.

The plate body 41 can further include first and second stop members, such as pairs of first and second stop members, that abut the securement head 54 when the securement member 50 is in the locked and unlocked configurations, respectively. Thus, abutment between the securement head 54 and the stop members in combination with abutment between the auxiliary shaft 62 and the stop surfaces 66 and 68, can distribute the load that prevents over-rotation of the securement member 50.

During operation, the securement member 50 can be in its unlocked configuration. The plate 40 can be brought toward the proximal end of the implant 20 until the securement head 52 is inserted through an opening 72 into an interior void 74 of the implant 20 that is partially defined by the retention wall 56. The opening 72 can be large enough to receive the securement head 52 when the securement member 50 is in the unlocked configuration, but not large enough to receive the securement head 52 when the securement member 50 is in the locked configuration. When the securement head 52 is disposed in the void 74, the securement member 50 can be iterated to the locked configuration whereby the securement head 52 is aligned with the retention wall 56 in the manner described above. The securement member 50 is then urged to travel in the securement direction until the retention wall 56 is captured between securement head 52 and the seat 58 in the manner described above.

Figures 7A, 7B:
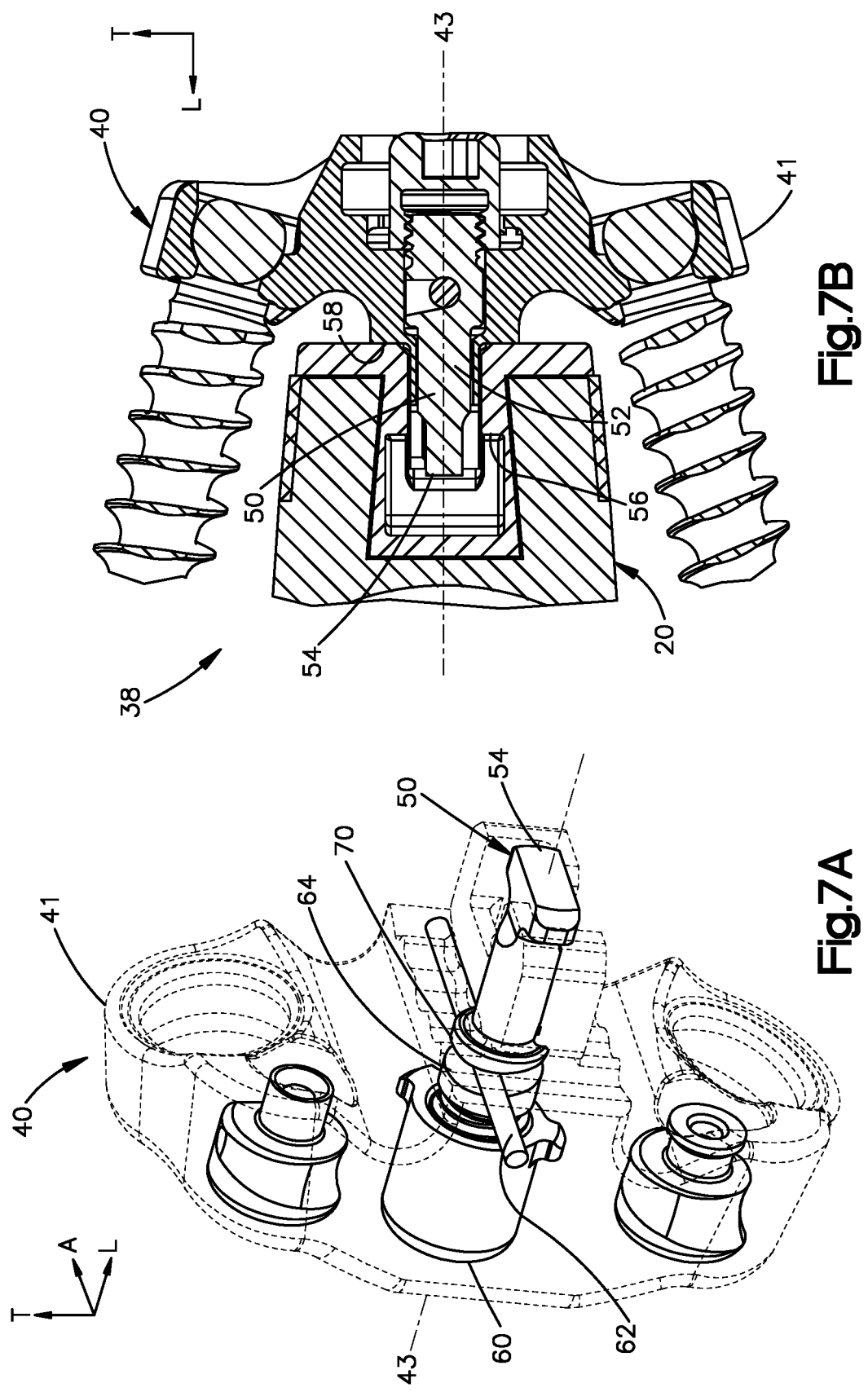
FIG. 7A is a perspective view of a plate constructed in accordance with yet another example, with portions cut away for the purposes of illustration.
FIG. 7B is a sectional side elevation view of the plate of FIG. 7A, shown inserted into an intervertebral implant.
Figures 7C, 8:
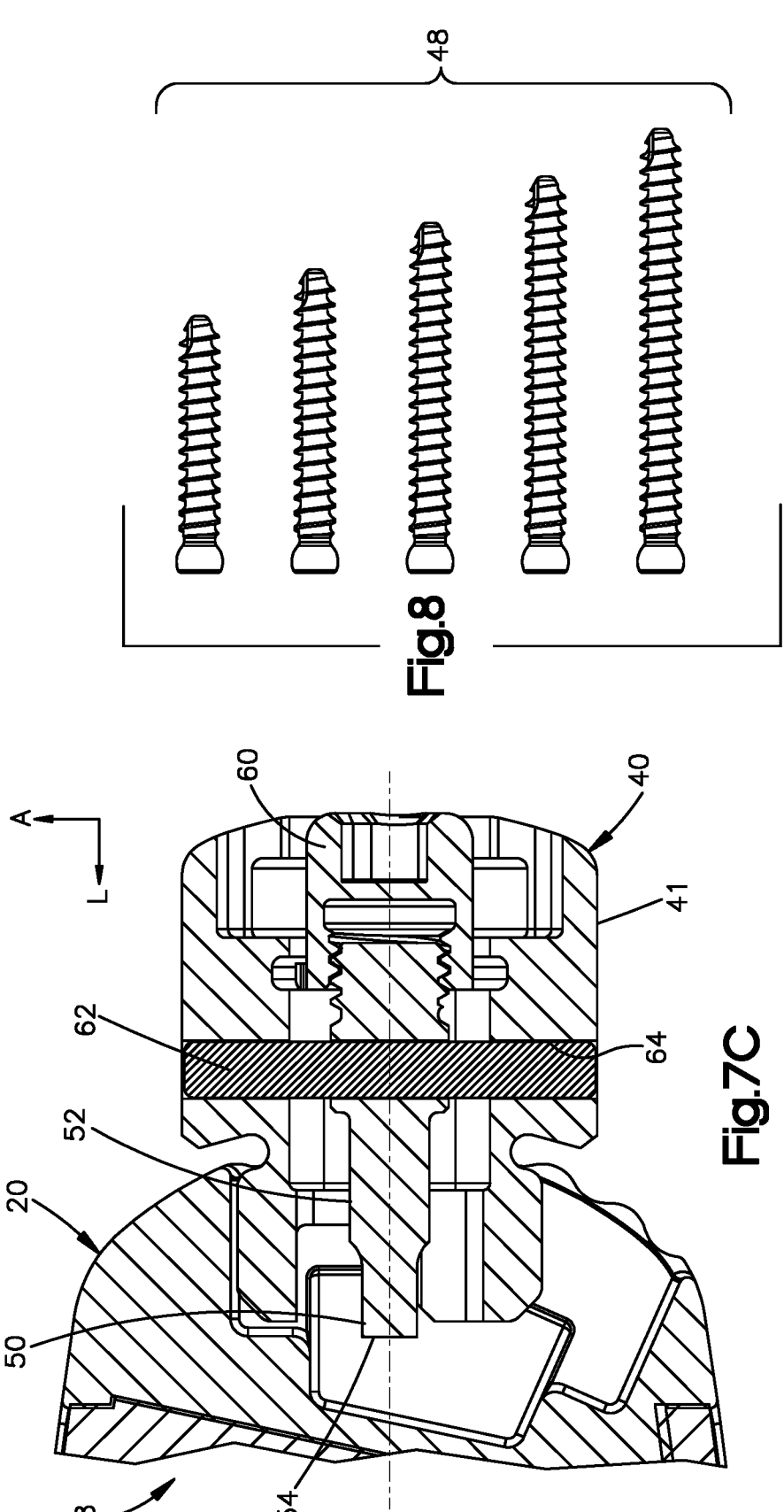
FIG. 7C is another cross-sectional view of the plate of FIG. 7A.
FIG. 8 shows a plurality of bone screws that can be included in a kit.

As illustrated in FIGS. 2A-2C, the auxiliary shaft 62 can extend from the plate body 41 into the slot 64 of the securement member 50. Thus, the auxiliary shaft 62 extends into but not through the securement shaft 52. Further, the auxiliary shaft 62 terminates without crossing the axis of rotation 43. The auxiliary shaft 62 can threadedly engage the plate body 41 so as to positionally fix the auxiliary shaft 62 with respect to the plate body 41. Alternatively, as illustrated in FIGS. 7A-7C, the auxiliary shaft 62 can be configured as a pin that extends across the axis of rotation 43 and can intersect the axis of rotation 43. In particular, the auxiliary shaft 62 can extend entirely through the securement member 50 and in particular through the securement shaft 52. Opposed ends of the auxiliary shaft 62 can be secured in the plate body 41. It should be appreciated that the auxiliary shaft can be described as extending at least into the securement member 50, meaning extending into or through the securement member 50. The auxiliary shaft 62 can be oriented substantially perpendicular to the axis of rotation 43.

Referring now to FIGS. 6A-6H, in still another example the securement member 50 can define an angled recess 76 that receives the auxiliary shaft 62 as the securement member 50 rotates 50 about the axis of rotation 43, which drives the securement member 50 to selectively travel proximally in the securement direction and distally in the disengagement direction. In particular, the recess 76 can extend along the longitudinal direction as it extends circumferentially about at least a portion of the outer periphery of the securement member 50 and in particular the securement shaft 52. The auxiliary shaft 62 interfaces with the securement shaft 52 so as to drive the securement member 50 to travel in the securement and disengagement directions selectively during rotation of the securement member 50.

During operation, the securement member 50 can be in the unlocked configuration, such that the securement head 54 can be inserted into the implant 20 in the manner described above. Next, the securement member 50 is rotated in the first direction of rotation, which causes the auxiliary shaft 62 to ride in the recess 76. The auxiliary shaft 62, in turn, drives the securement member 50 to translate along the axis of rotation 43. In particular, rotation of the securement member 50 in the first direction of rotation causes the auxiliary shaft 62 to drive the securement member 50 to translate in the proximal securement direction until the retention wall 56 is captured between the securement head 54 and the seat 58 as described above. It is recognized that because the retention wall 56 is aligned with the auxiliary head 54 along the longitudinal direction L, the securement head 54 can be said to be in the locked configuration. Conversely, rotation of the securement member 50 in the second direction of rotation causes the auxiliary shaft 62 to drive the securement member 50 to translate in the distal disengagement direction which causes the securement head 54 to move away from the retention wall 56 until the securement member 50 is in the unlocked configuration whereby the securement head 54 can be removed from the implant 20 by moving the plate 40 in the proximal direction relative to the implant 20.

While the auxiliary shaft 62 rides in the recess 76 in one example, it should be appreciated that the recess 76 is only one example of any suitable track that can couple to the auxiliary shaft 62. The auxiliary shaft 62 can ride along the track while positionally fixed to the plate body 41, thereby driving the securement member 50 to rotate to the locked configuration and the unlocked configuration as it travels in the securement direction and the disengagement direction, respectively. In one example, the track can be a helical track or can have any suitable alternative shape as desired that causes the securement member to travel along the axis of rotation 43 as it rotates about the axis of rotation 43.

Referring again to FIGS. 1A and 2A, the plate 40 can be angularly and translatably adjustable along an adjustment surface 25 that is disposed at the proximal or trailing end 24 of the intervertebral implant 20 between a plurality of positions at which the plate 40 is configured to secure to the implant 20. The positions can be translationally offset from each other along a horizontal plane, and can further be angularly offset with respect to each other along the horizontal plane. The horizontal plane can be perpendicular to the transverse direction T, and thus defined by the longitudinal direction L and the lateral direction A. The adjustment surface 25 can be generally convex in the horizontal plane. The plate 40 can define a complementary concave adjustment surface 45 that is configured to engage the adjustment surface 25 of the implant 20. Each of the adjustment surfaces 25 and 45 can be scalloped so as to intermesh with each other when the plate 40 is positioned at one of the plurality of positions. Because the adjustment surface 25 is curved, the angle of the plate 40 is adjusted as the plate translates along the adjustment surface 25. It should be appreciated that the plate 40 can be secured to the implant as described above to releasably lock the plate at the position among the plurality of positions. The different angles at the various positions can be up to forty five degrees, including up to thirty degrees positions. In one example, the plate 40 is configured to be secured at any angle as desired, such as approximately zero degrees, approximately fifteen degrees, and approximately thirty degrees as defined by the axis of rotation 43 and the insertion direction of the implant 20.

Figures 3A, 3B, 3C, 4A, 4B, 4C, 5A, 5B, 5C:
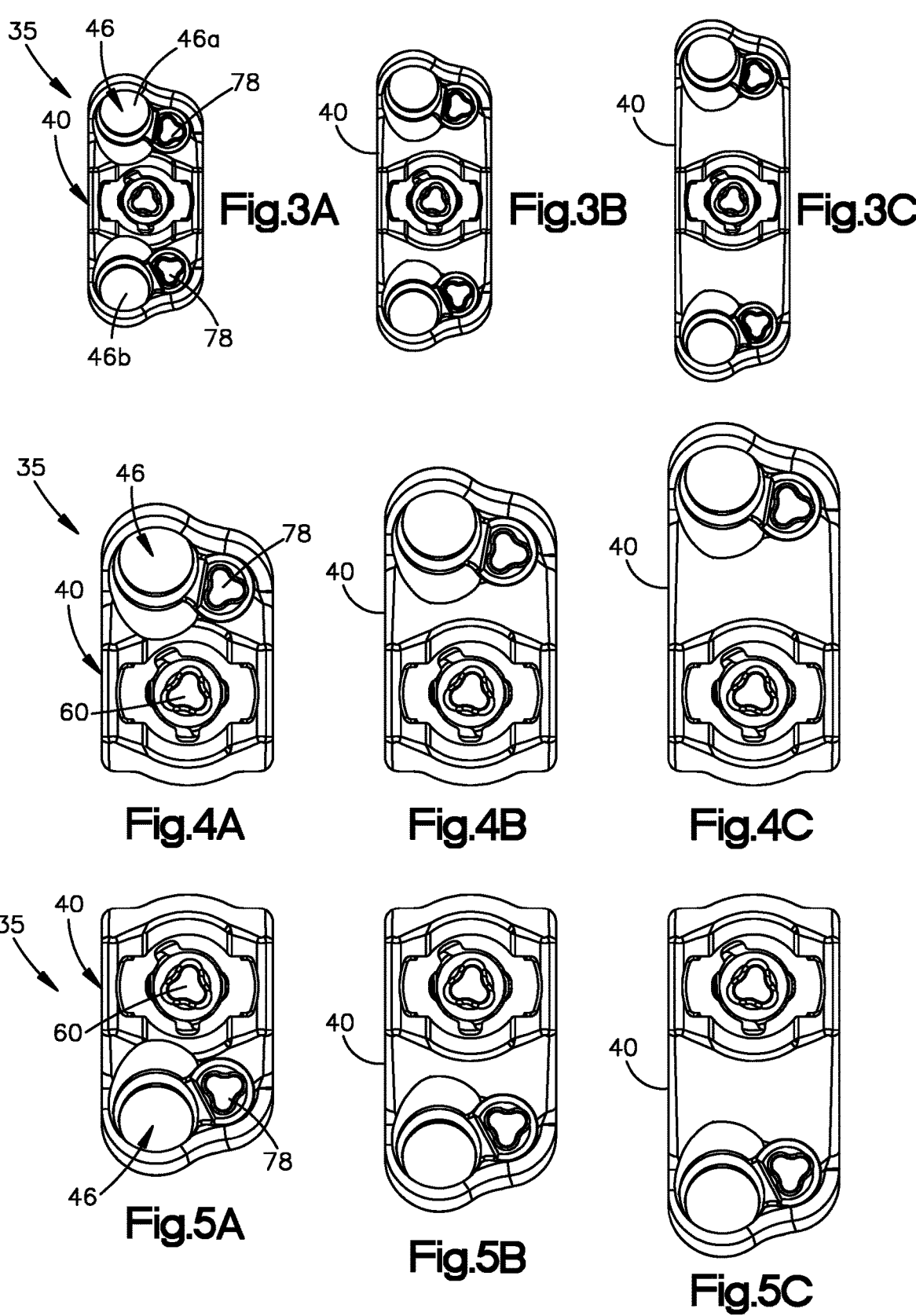
FIG. 3A is a plan view of a plate having a pair of screw holes.
FIG. 3B is a plan view of the plate of FIG. 3A but having a different size.
FIG. 3C is a plan view of the plate of FIGS. 3A-3B but having a different size.
FIG. 4A is a plan view of a plate having a screw hole in a first orientation.
FIG. 4B is a plan view of the plate of FIG. 4A but having a different size.
FIG. 4C is a plan view of the plate of FIGS. 4A-4B but having a different size.
FIG. 5A is a plan view of a plate having a screw hole in a second orientation different than the first orientation of FIG. 4A.
FIG. 5B is a plan view of the plate of FIG. 5A but having a different size.
FIG. 5C is a plan view of the plate of FIGS. 5A-5B but having a different size.
Figure 6A:
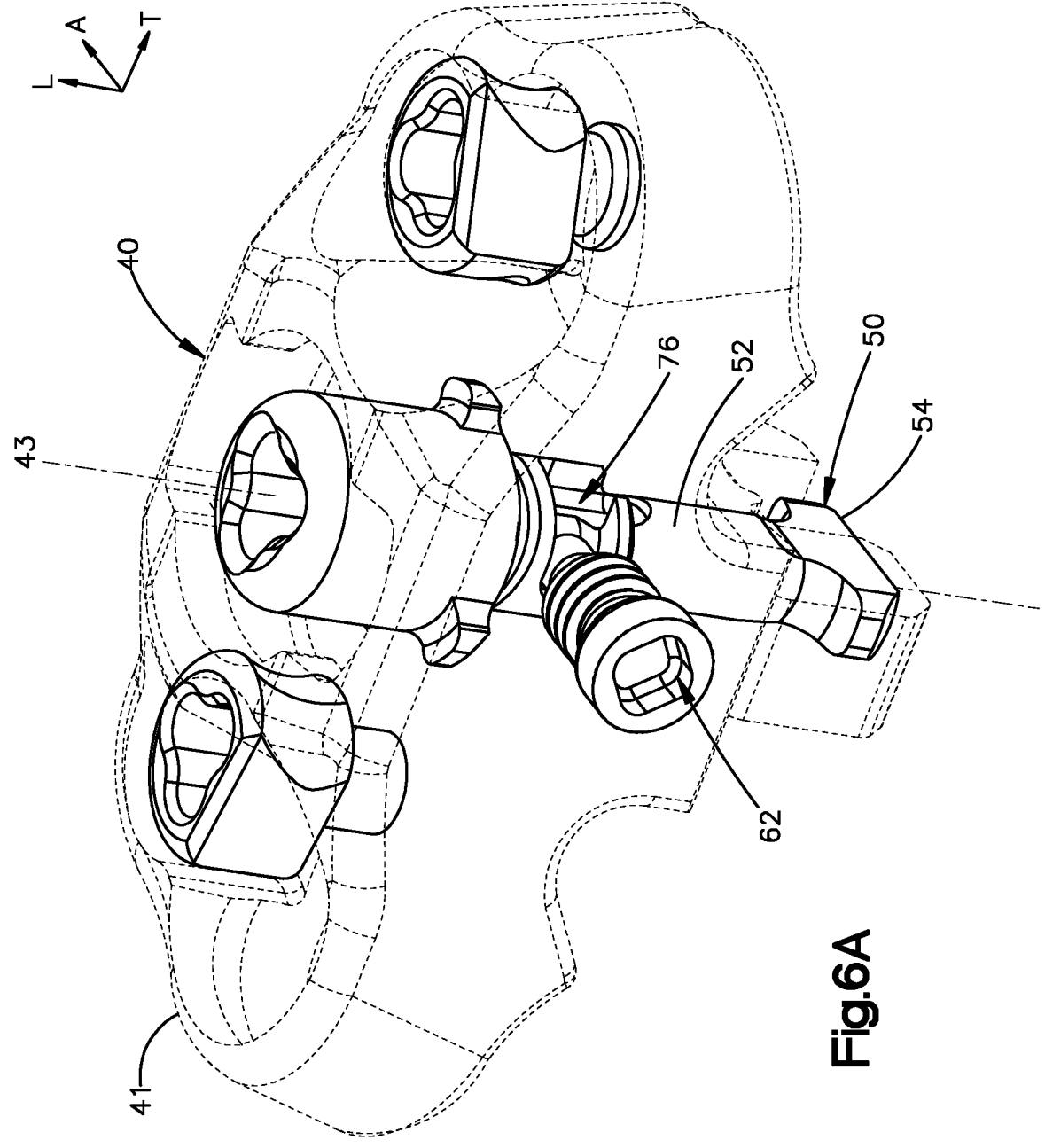
FIG. 6A is a perspective view of a plate constructed in accordance with another example, with portions cut away for the purposes of illustration.
Figures 6B, 6C, 6D, 6E:
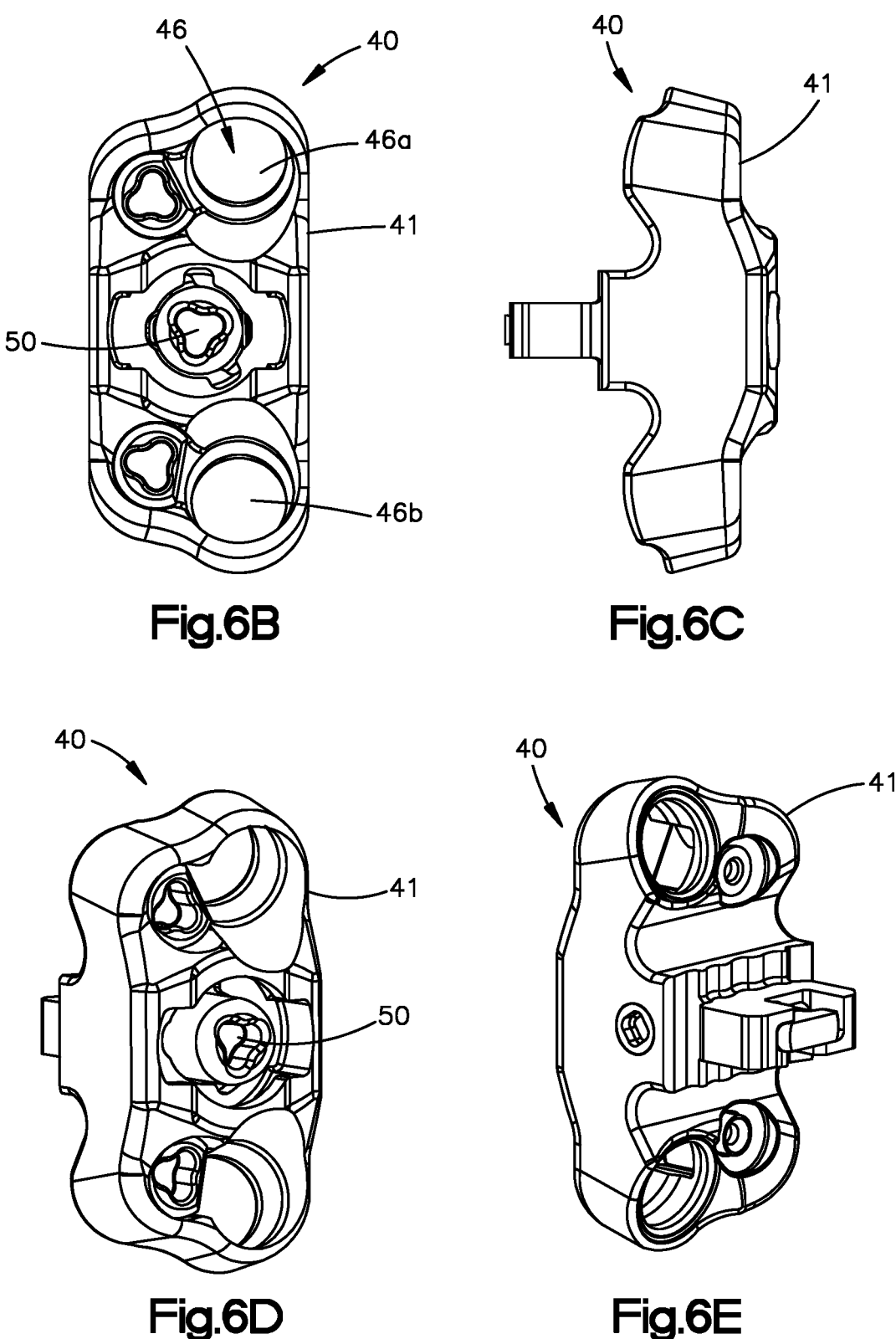
FIG. 6B is a front elevation view of the plate of FIG. 6A.
FIG. 6C is a side elevation view of the plate of FIG. 6A.
FIG. 6D is a front perspective view of the plate of FIG. 6A.
FIG. 6E is a rear perspective view of the plate of FIG. 6A.
Figure 6F:
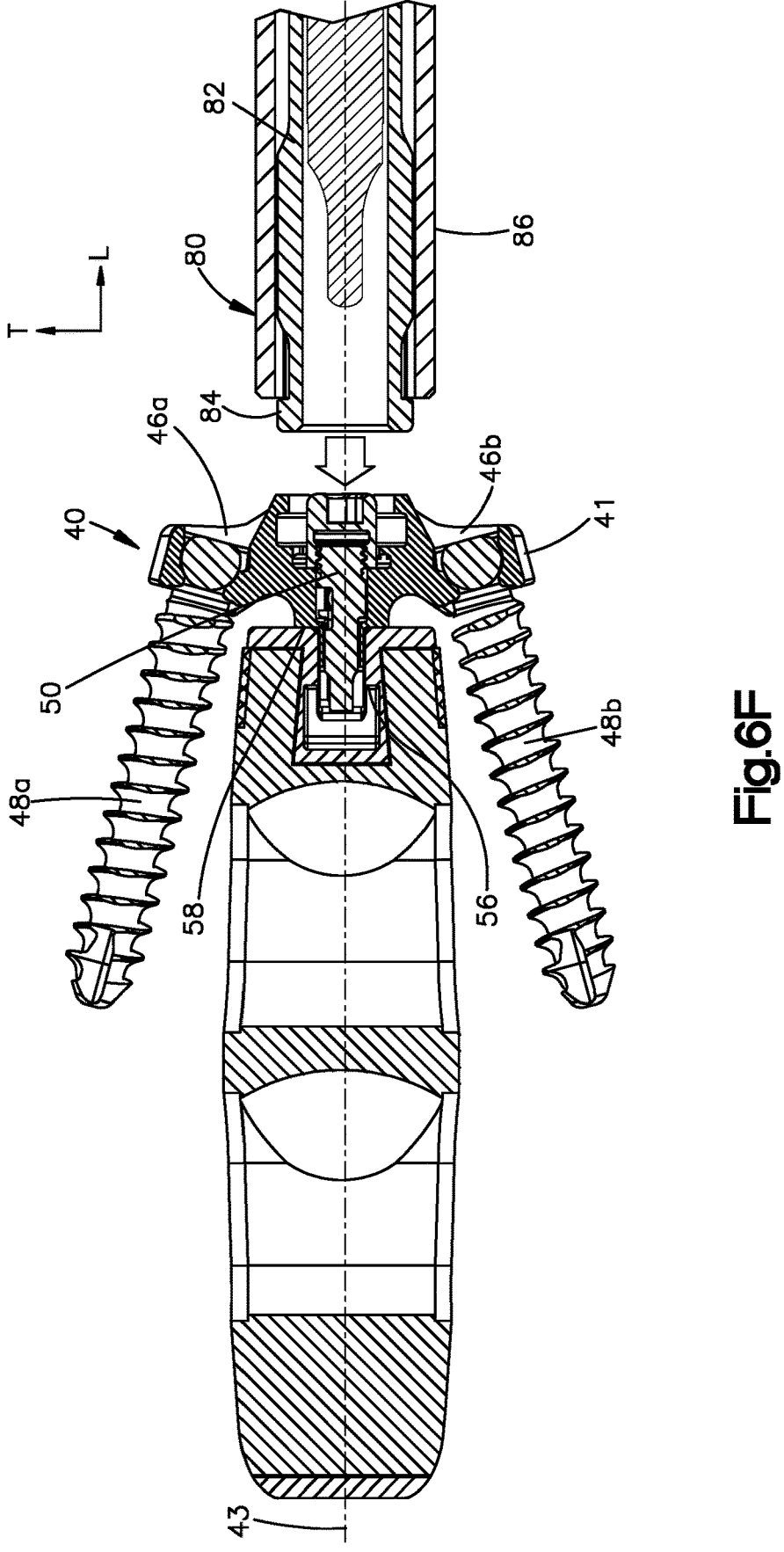
FIG. 6F shows an inserter instrument aligned to be coupled to the plate that has been inserted into an intervertebral implant in an unlocked configuration.
Figure 6G:
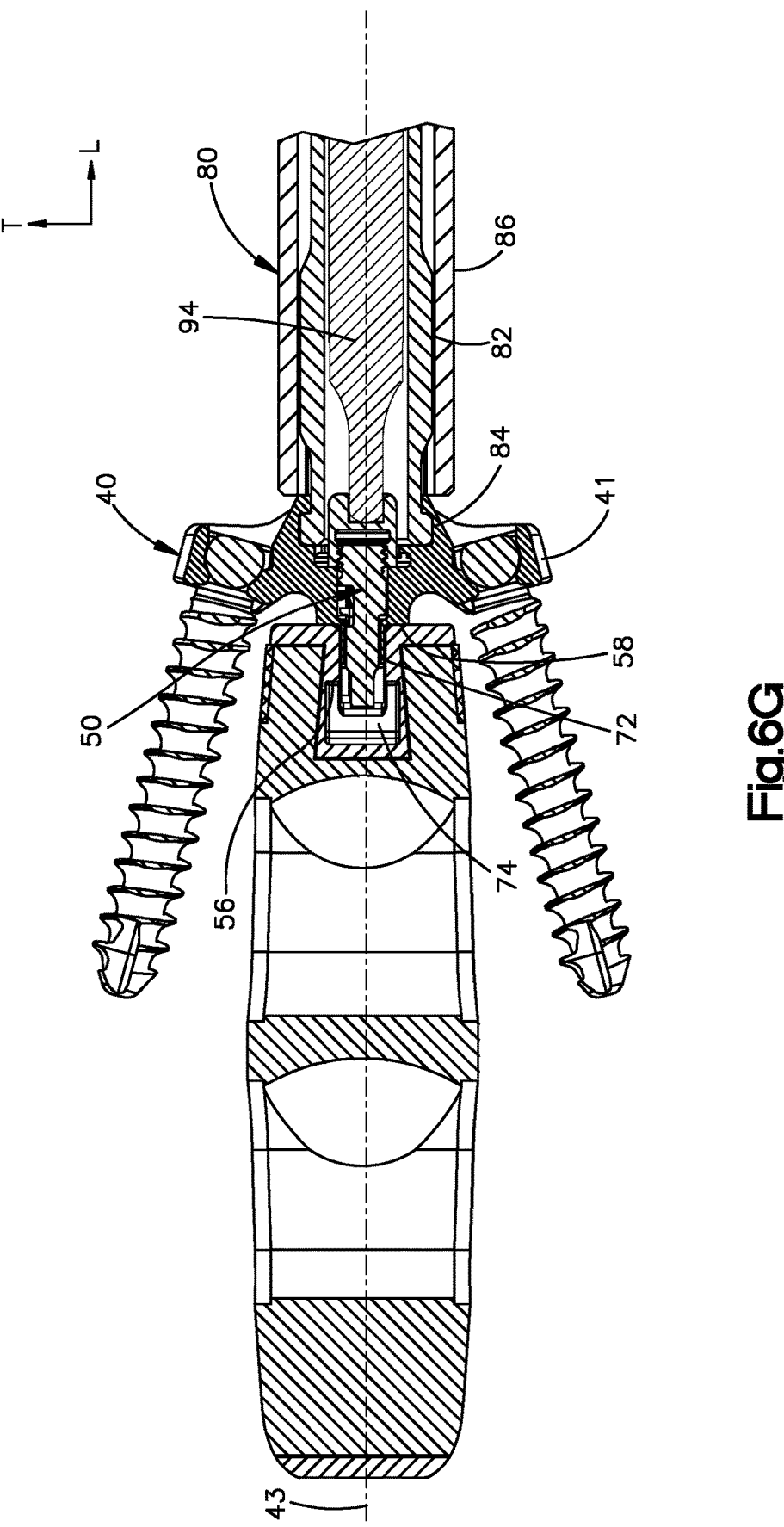
FIG. 6G shows a driver instrument inserted through the inserter instrument, after the driver instrument has driven a securement member of the plate from an unlocked configuration to a locked configuration.
Figure 6H:
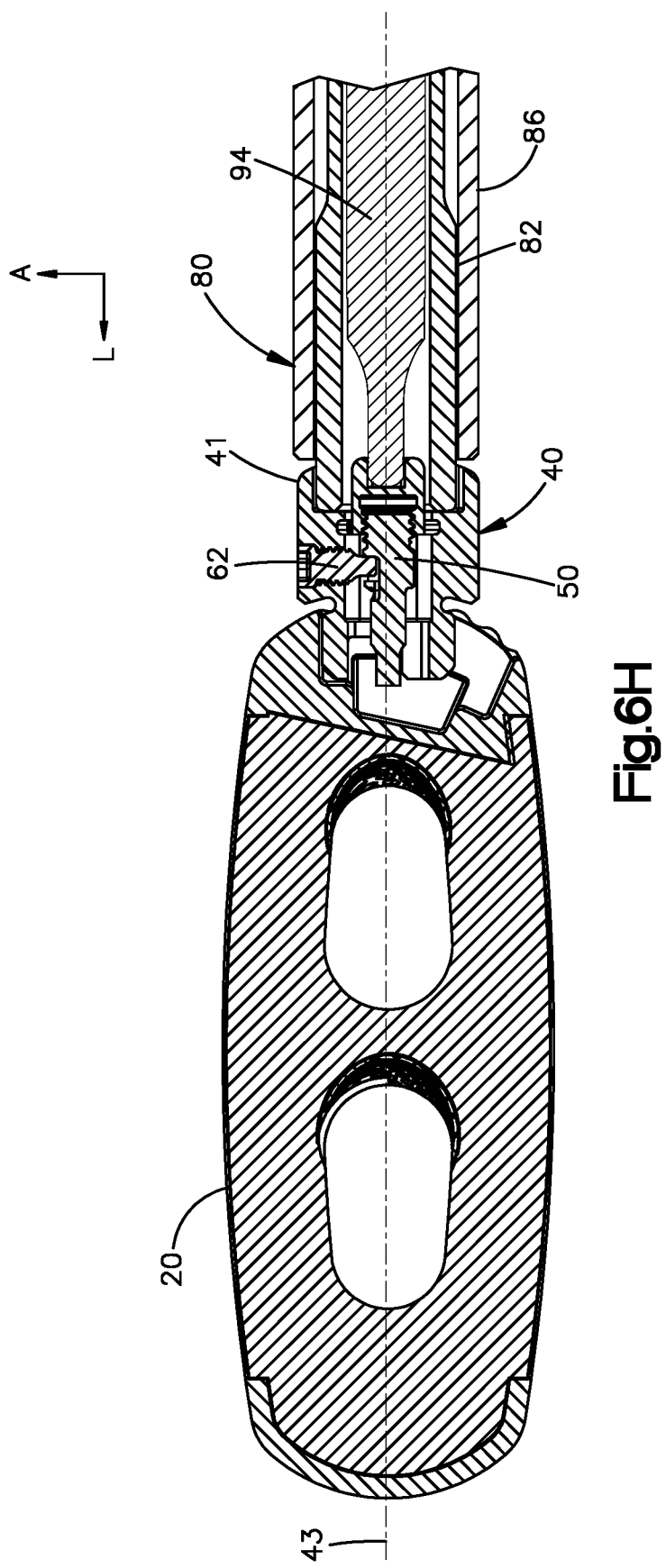
FIG. 6H is another cross-sectional view of the driver shown coupled to the securement member.

Referring now to FIGS. 3-5, a kit 35 can include a plurality of plates 40 as described above, but with different numbers of bone fixation holes 46 and/or bone fixation holes 46 positioned at different relative locations. For instance, as shown at FIGS. 3A-3C and described above, the plate can include first and second bone fixation holes 46a and 46b. In other examples shown in FIGS. 4A-4C and 5A-5C, the plates 40 can each include only a single bone fixation hole 46. The plate 40 can be oriented in a first orientation so as to couple and secure to the implant 20 with the fixation hole 46 aligned with the superior vertebral body. Alternatively, the plate 40 can be oriented in a second orientation so as to couple and secure to the implant 20 with the fixation hole aligned with the superior vertebral body.

A first one plate or first plurality of plates 40 of the kit 35 can include a respective single bone fixation hole 46 at a first position as shown at FIGS. 4A-4C, and a second one plate or a second plurality of plates 40 of the kit can include a respective single bone fixation hole at a second position different than the first location as shown at FIGS. 5A-5C. Thus, when the first and second plates 40 are overlayed on each other so that their respective outer perimeters are aligned, the respective bone fixation holes 48 will be out of alignment. In one example, the first plates 40 can be mirror images with respect to the second plates. The kit can include a third one plate or a third plurality of plates 40 having the first and second bone fixation holes 46a and 46b as described above. Further, the kit can include the plates 40 of FIGS. 3, 4, and 5 of different sizes. Referring now to FIG. 8, the kit can further include bone fixation elements 48 that can be configured as bone screws of different lengths that are configured to be inserted through the bone fixation holes 46 of the plates 40 of the kit and into underlying bone.

Referring now again to FIGS. 1A and 3A-5C, each of the plates 40 described herein can include a cam member 78 associated with each bone fixation hole 46 and is movable from a first position that is spaced from a head of the bone fixation element to a second position whereby the cam member interferes with the head so as to prevent back-out of the bone fixation element. Thus, the bone fixation element 48 can be inserted through the fixation hole 46 while the cam member 78 is in the first position, and the cam member 78 can subsequently be moved to the second position. In one example, the cam member 78 can be rotated from the first position to the second position. For instance, the cam member 78 can be rotated about an axis that is oriented along the longitudinal direction L. As the cam member 78 moves to the second position, an inner surface of the cam member 78 can move toward the head of the bone fixation element 48 until the inner surface overlies the head of the bone fixation element 48. Further, the cam member 78 can apply retention force against the head of the bone fixation element 48 that urges the bone fixation element 48 toward the underlying bone in its insertion direction into the bone when the cam member is in the second position.

Figures 9A, 9B:
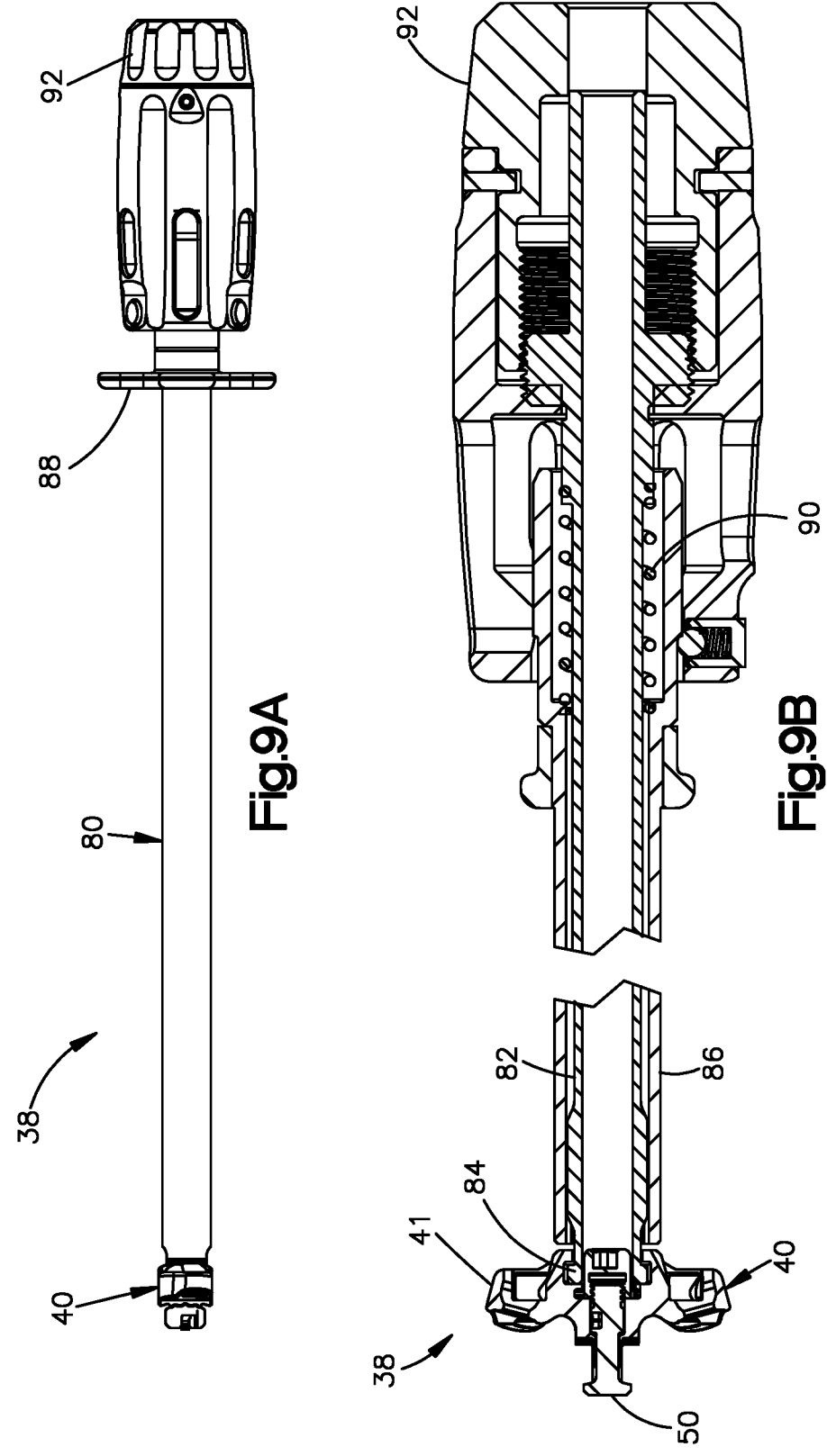
FIG. 9A is a side elevation view of a plate inserter.
FIG. 9B is a sectional side elevation view of the plate inserter of FIG. 9A, shown with portions removed.

It should be appreciated that the bone fixation system 38 can include the plate 40 and the implant 20. Further, the kit can include a plurality of implants 20 of different sizes and lordotic profiles. Referring now to FIGS. 9A-9B, the bone fixation system 38 can further include an inserter 80 that is configured to couple to the plate 40. The inserter 80 can include an inner sleeve 82 having a plate-engaging end 84, and an outer sleeve 86 that surrounds the inner sleeve and is coupled to an engagement member 88 that is movable in the rearward direction to correspondingly move the outer sleeve 86 rearwardly from the plate-engaging end 84 of the inner sleeve 82. The engagement member 88 can, in some examples, be moved manually in the rearward direction so as to expose the plate-engaging end 84 of the inner sleeve 82. The plate-engaging end 84 is configured to be inserted into a groove of the plate body 41 along an insertion direction, and subsequently rotated along a direction of rotation to a position whereby the plate-engaging end 84 interferes with one or more flanges of the plate body 41 so as to prevent backout of the inner sleeve 82 from the plate body 41 along a direction opposite the insertion direction, thereby coupling the inserter 80 to the plate body 41. The direction of rotation can be about the insertion direction. Subsequently releasing the engagement member 88 can cause the outer sleeve 86 to travel forward so as to engage the plate body 41 and prevent relative rotation between the inserter 80 and the plate body 41. The outer sleeve 86 can be spring loaded, such that moving the engagement member 88 in the rearward direction is against a spring force of a spring 90 that biases the outer sleeve 86 in the forward direction. Thus, releasing the engagement member 88 causes the outer sleeve 86 to move in the forward direction under the force of the spring 90. An actuator 92, configured as an end cap in one example, can be rotated to tighten the interface between the plate body 41 and the inner and outer sleeves 82 and 86.

In one example, the forward direction can be defined by the distal direction, and the rearward direction can be defined by the proximal direction.

Figures 10A, 10B:
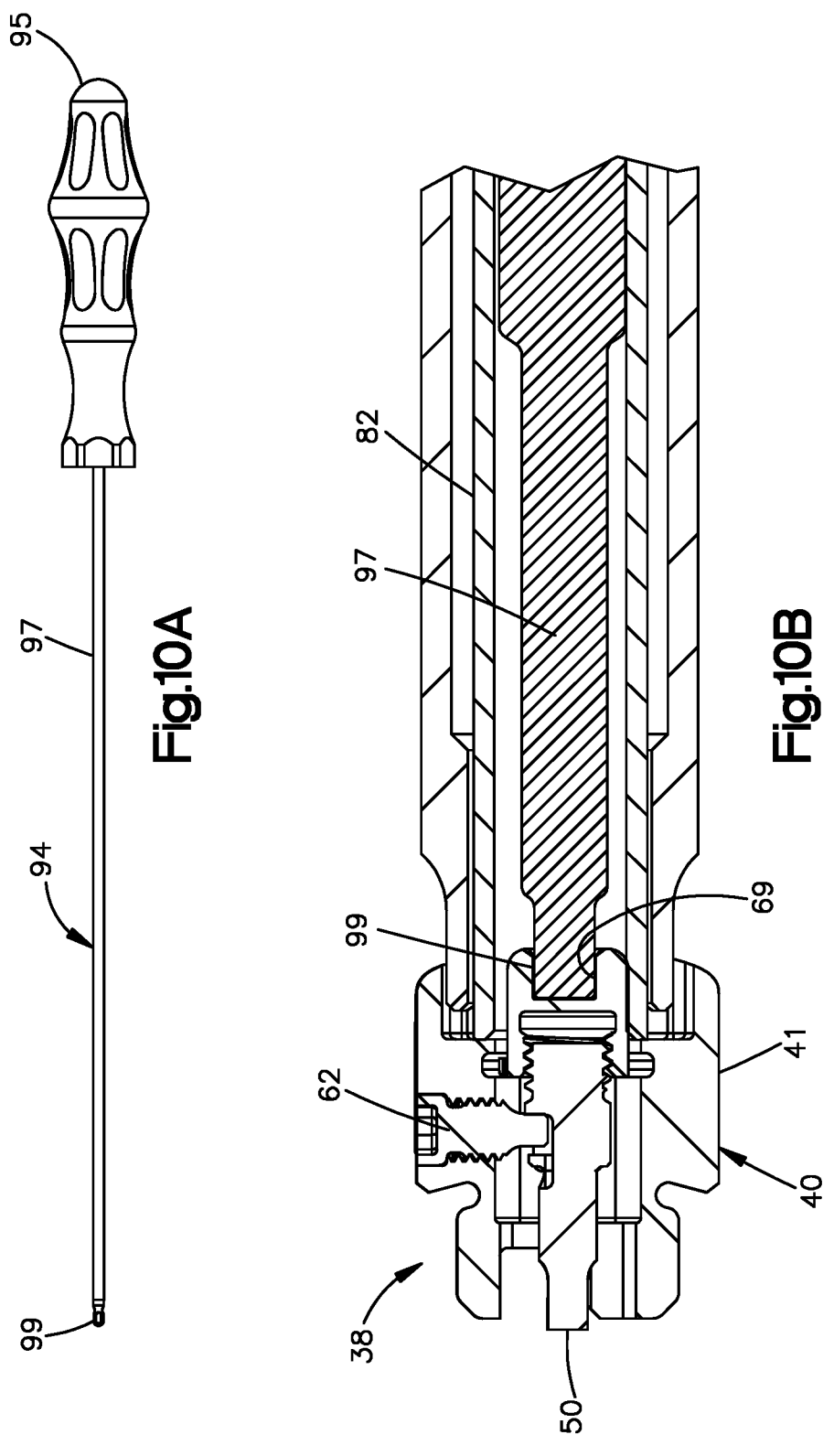
FIG. 10A is a side elevation view of a driver configured to be inserted in the inserter of FIGS. 9A-9B.
FIG. 10B is a sectional side elevation view of a portion of the driver of FIG. 10A shown operably coupled to a plate.

Referring now also to FIGS. 10A-10B, the bone fixation system 38 can further include a driver instrument 94 that is configured to be received by, or otherwise coupled to, the inserter 80. In particular, the inner sleeve 82 of the inserter 80 can be cannulated such that the securement member 50 or actuator 60 is exposed in the cannula. The securement member 50 or actuator can include a rear-facing interface that is configured to receive the driver instrument 94 that is configured to drives the securement member 50 or actuator 60 to rotate in the manner described above between the unlocked configuration and the locked configuration. The driver instrument 94 can include a handle 95 and a shaft 97 that extends distally from the handle 95 and is configured to be inserted into the inner sleeve 82 and driven distally until an engagement end 99 of the driver instrument couples with the securement member 50 or actuator 60. The engagement end 99 can be defined by the shaft 97, and in particular as a distalmost portion of the shaft 97. In one example, the engagement end 99 of the driver instrument 94 can be received in a suitably shaped socket 69 of the securement member 50 or actuator 60. The inserter 80 can provide a counter torque to the plate body 41 while the driver instrument 94 drives the securement member 50 or actuator 60 to rotate.

As shown in FIGS. 11A-11B, the inserter 80 can be coupled to the plate 40, and the driver instrument 94 can secure the plate 40 to the implant 20 to produce a rigid construct prior to inserting the implant 20 in the intervertebral space 51. Alternatively, the implant 20 can be first inserted into the intervertebral space 51, and the inserter 80 can then couple to the plate 40, and the driver instrument 94 can then secure the plate 40 to the implant 20 in the manner described herein.

Figures 12A, 12B:
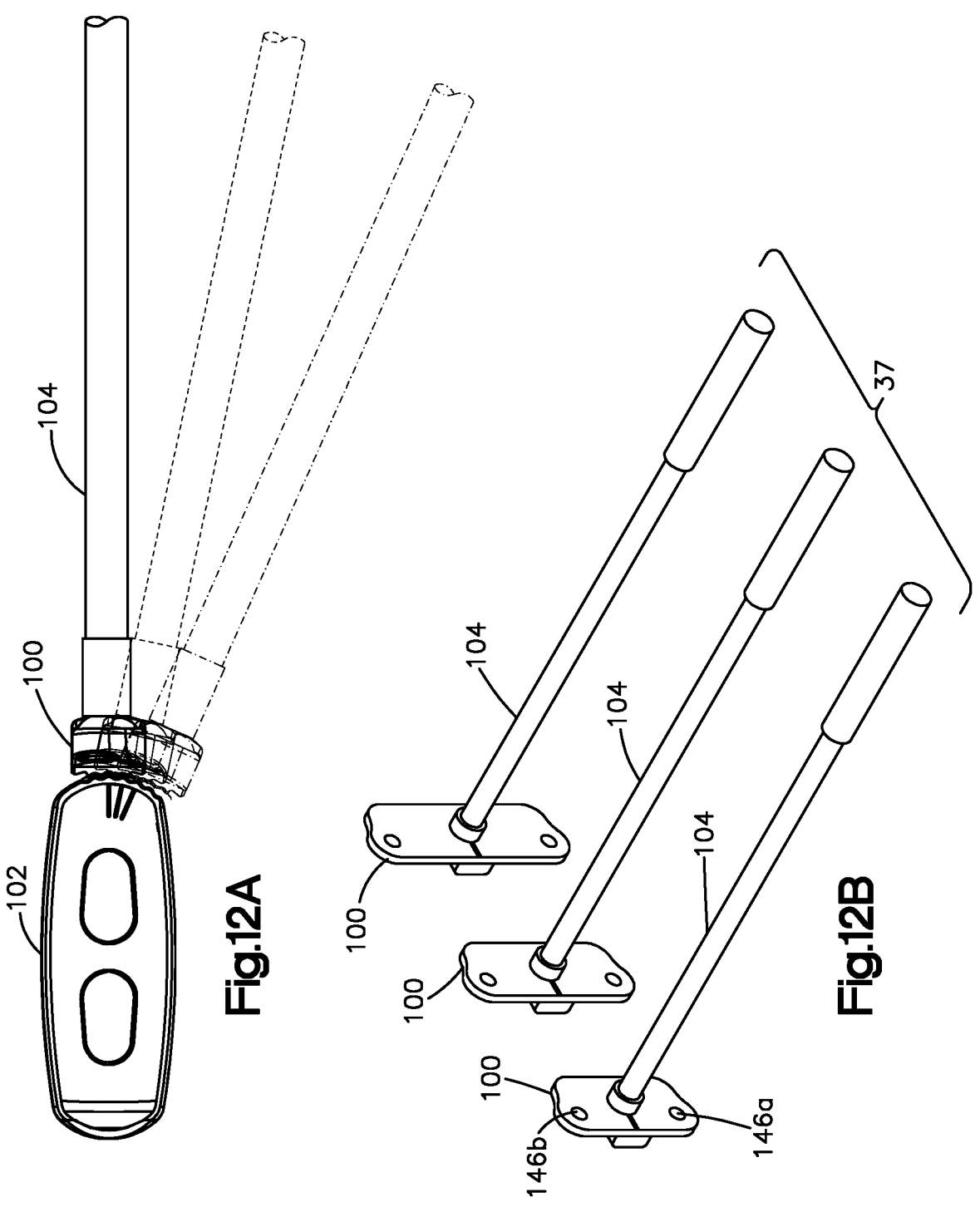
FIG. 12A shows a kit including a trial plate attached to a trial implant, and a trial inserter attached to a trial plate in one of multiple angular positions.
FIG. 12B shows the kit including a plurality of differently sized trial plates attached to respective trial inserters.

Referring now to FIG. 12A-15 in generally, a trial kit 37 can include trial plates 100 corresponding to each of the plates 40 described herein with respect to FIGS. 3-5, and one or more trial implants 102 that correspond to the intervertebral implants 20 described above. The trial kit 37 including the trial plates 100 and trial implants 102 can be included in the kit 35 described above, or can be a separate kit as desired. The trial plates 100 can be brought against a trial implant 102 or permanent implant to determine the proper sized plate 40 to be secured to the implant. The trial plates 100 can be coupled to or monolithic with a trial insertion member 104 that is configured to be received in the internal void of the trial implant so as to simulate the securement member 50 in the unlocked configuration. The trial insertion member 104 can further be positioned at one of a plurality of different angles described above to determine the proper plate 40 and the proper angle at which to couple the proper plate 40 to the implant 20 within the range of angles. For instance, as shown at FIG. 12A, the insertion member 104 can be oriented at any suitable angle as desired along a plane defined by the anterior-posterior direction and the medial-lateral direction. As shown at FIG. 12B, the trial plates 100 can be differently sized, and can include respective first and second fixation holes 146a and 146b spaced apart from each other by different distances that can positionally correspond to the fixation holes 46a and 46a of the final plate 40 to be implanted.

Figures 13A, 13B, 13C:
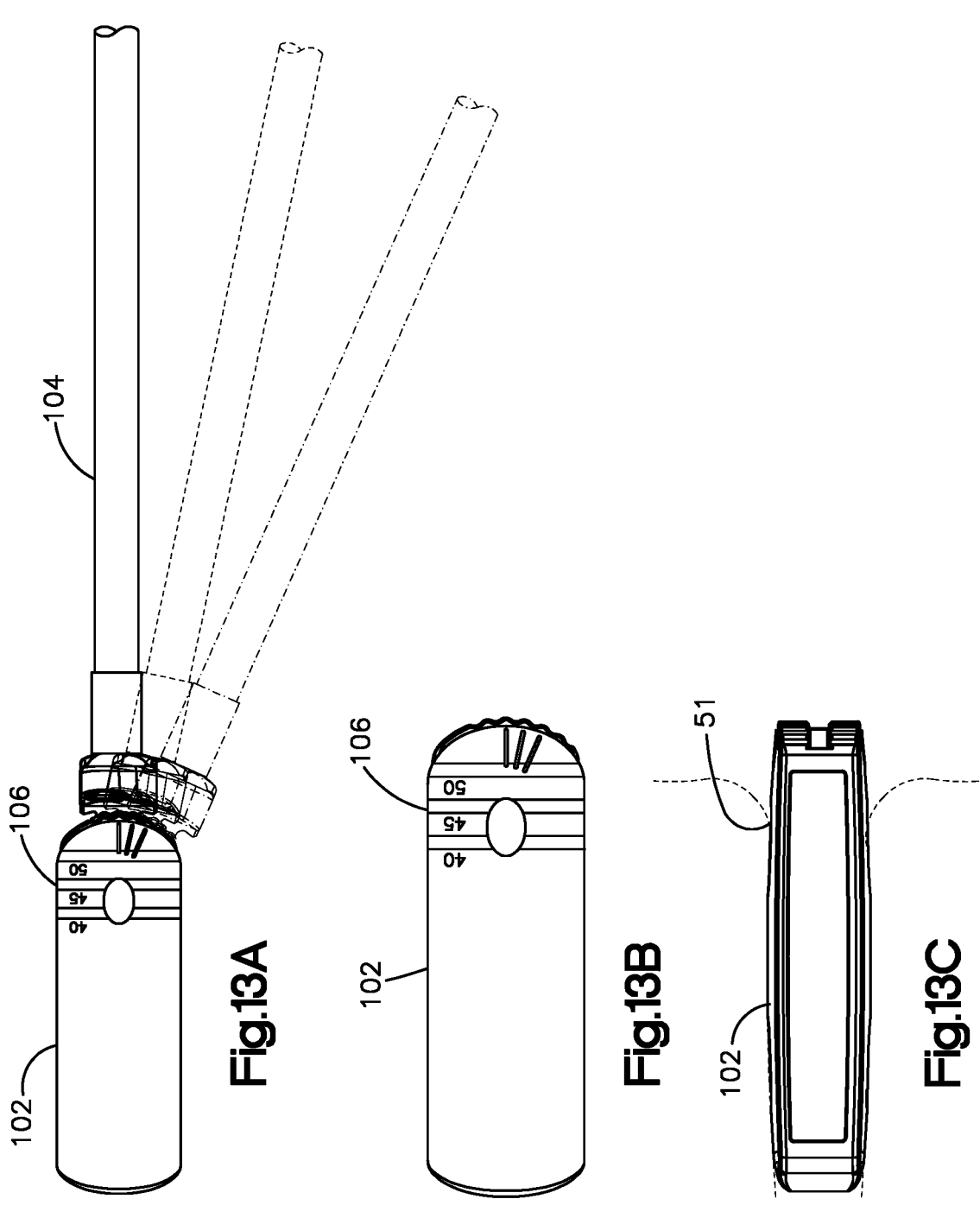
FIG. 13A shows the kit including a trial plate attached to a trial implant, and a trial inserter attached to a trial plate in one of multiple angular positions, wherein the trial plate includes insertion depth markings.
FIG. 13B is a top plan view of the trial implant of FIG. 13A.
FIG. 13C is a side elevation view of the trial implant of FIG. 13B inserted into an intervertebral space.
Figures 14A, 14B, 14C, 14D:
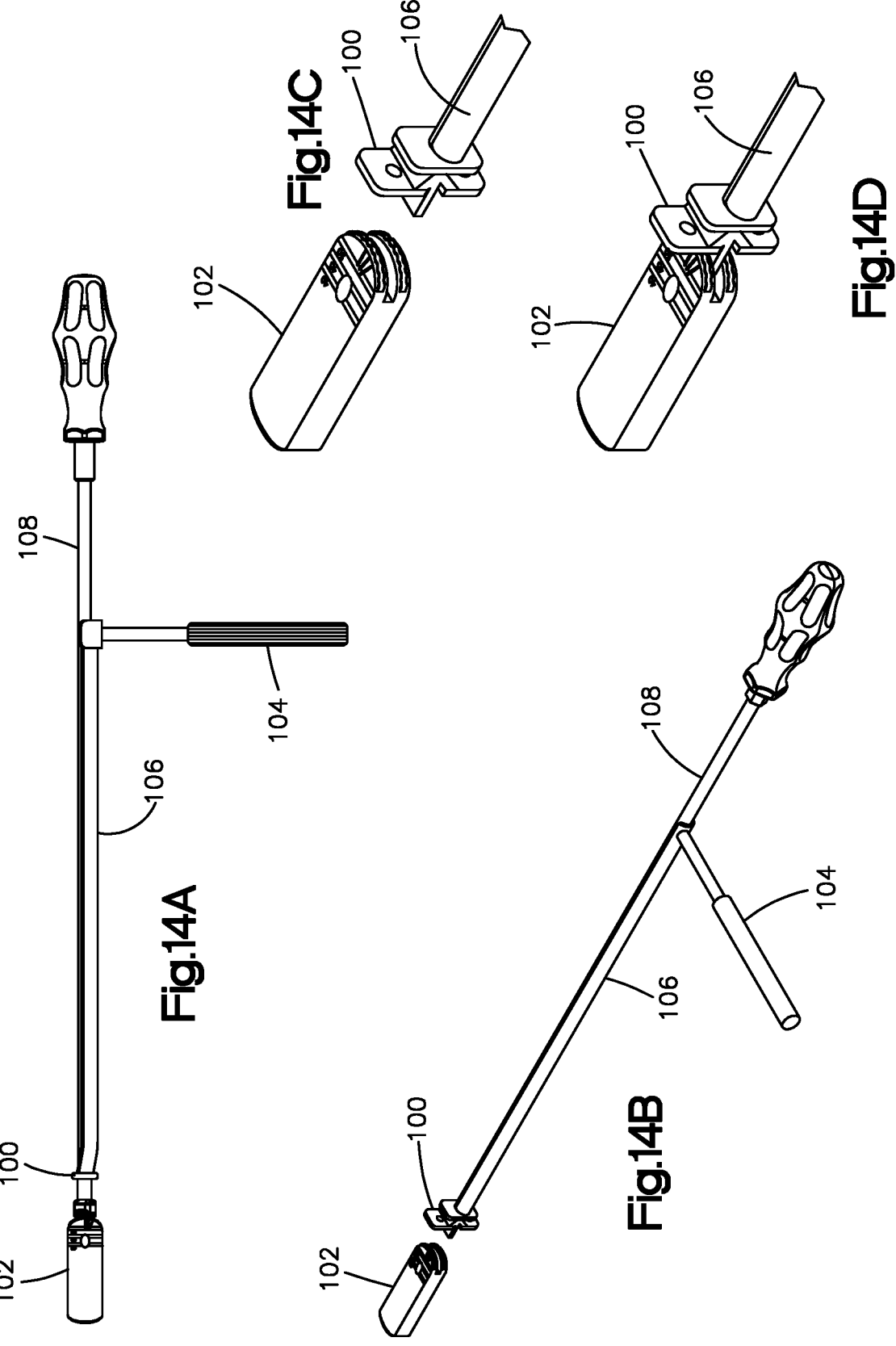
FIG. 14A shows a trial implant inserter coupled to a trial implant, and a trial insertion member coupled to a trial plate, wherein the trial insertion member partially surrounds the trial implant inserter.
FIG. 14B shows the assembly of FIG. 14A, wherein the trial implant is shown exploded from the trial implant inserter.
FIG. 14C is an enlarged view of the trial implant, the trial plate, and a portion of the trial insertion member shown in FIG. 14C.
FIG. 14D shows the enlarged view of FIG. 14C, but shows the trial implant coupled to the trial implant inserter.

Referring to FIGS. 13A-13C, the trial implant 102 can include insertion depth markings 106. When the trial implant 102 is inserted and fully seated into the intervertebral space 51, the depth markings 106 indicate an insertion depth of the trial implant. Thus, a properly sized final implant 20 can be selected having the measured insertion depth of the trial implant, or an insertion depth that otherwise corresponds to the measured insertion depth of the trial implant.

Referring now to FIGS. 14A-14D, the trial kit 37 can further include a trial implant inserter 108 that can be removably attachable to the trial implants 102 or monolithic with respective ones of the trial implants 102. The trial implant inserter 108 can deliver the trial implant 102 into the intervertebral space 51. The trial insertion member 104 can be configured as a sleeve 106 that at least partially surrounds the trial implant inserter 108 so as to position the trial plate 100 with respect to the trial implant 102 as desired. In this manner, a desired size and configuration of the final intervertebral implant 20 and the final plate 40 can be determined.

Figures 15A, 15B, 15C, 15D, 15E, 15F:
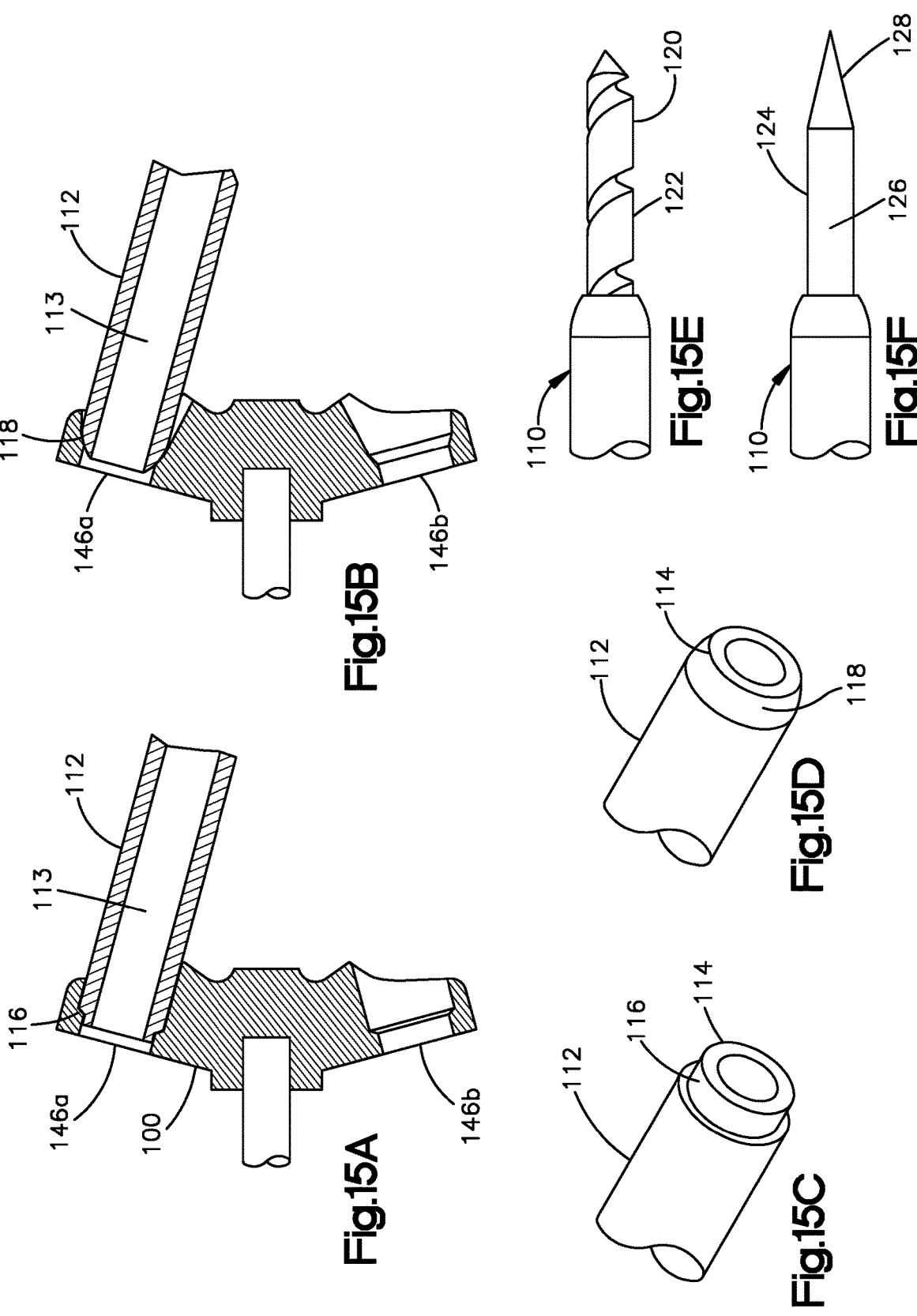
FIG. 15A shows a guide sleeve inserted into a fixation hole of the trial plate at a fixed angle.
FIG. 15B shows a guide sleeve inserted into a fixation hole of the trial plate at a variable angle.
FIG. 15C is a perspective view showing an interlock end of the guide sleeve shown in FIG. 15A.
FIG. 15D is a perspective view showing an articulation surface of the guide sleeve of FIG. 15B.
FIG. 15E shows an opening device configured as a drill in one example.
FIG. 15F shows an opening device configured as an awl in another example.

Referring now to FIGS. 15A-15F, any suitable opening instrument 110 can be driven through the fixation holes 146a and 146b of the trial plane 100 to produce pilot holes in the underlying bone for the later insertion of the bone screws through the fixation holes 46a and 46b of the final plate 40 in the manner described above. The trial kit 37 can further include one or more guide sleeves 112 that are configured to be inserted into either or both of the fixation holes 146a and 146b. Each of the guide sleeves 112 can define an inner surface that defines a through hole 113, and an outer surface opposite the inner surface. The opening instrument 110 can be driven through the through hole 113, such that the inner surface guides the opening instrument 110 to the underlying bone so as to create the pilot hole in the underlying bone. The guide sleeve 112 can define an insertion end 114 that is configured to be selectively driven into the fixation holes 146a and 146b. The insertion end 114 can define an interlock 116 as shown in FIG. 15C, which can be inserted into the fixation hole so as to positionally lock the guide sleeve 112 in the fixation hole. Therefore, the opening instrument 110 creates the pilot hole along a fixed trajectory that is defined by the fixed angle of the guide sleeve 112. Alternatively, the insertion end 114 can define an articulation surface 118 that can be rounded or otherwise shaped so as to articulate along an internal surface of the trial plate 110 that defines the fixation hole. It is appreciated that the guide sleeve 112 angulates in the fixation hole relative to the trial plate 100 when the articulation surface 118 articulates, thereby correspondingly adjusting the trajectory of the pilot hole created in the underlying bone. As shown in FIGS. 15E-15F, the opening instrument 110 can be configured as a drill 120 having cutting flutes 122 in one example. Alternatively, the opening instrument 110 can be configured as an awl 124 having a smooth outer surface 126 and tapered tip 128. It should be appreciated that the opening instrument 110 can be alternatively configured as desired.

It is recognized that the plates described herein can provide stability to the intervertebral implant so as to resist or prevent migration of the implant as the patient is repositioned during the surgical procedure, for instance from from a lateral decubitus position to a prone position. It is appreciated that the additional posterior fixation, such as pedicle screws and one or more spine rods and the like can be implanted when the patient is in the prone position.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A plate configured to secure to an intervertebral implant that extends in a distal direction from the plate, the plate comprising:
   a plate body having at least one bone fixation hole configured to receive a bone fixation element that is driven into a vertebral body, wherein the plate body defines a seat;
   a securement member is configured to rotate in a first direction of rotation about an axis of rotation from an unlocked configuration to a locked configuration, wherein the securement member is configured to be driven to translate in a securement direction along the axis of rotation to a secured position until a retention wall of the intervertebral implant is captured between the seat and the securement member when the securement member is in the locked configuration; and
   an actuator that is configured to rotate in the first direction of rotation to drive the securement member to rotate in the first direction of rotation to the locked configuration, whereby continued rotation of the actuator in the first direction of rotation causes the securement to translate in the securement direction.

2. The plate of claim 1, wherein the securement member comprises a securement shaft and a securement head, wherein the securement head is configured to be inserted into the implant when the securement member is in the unlocked configuration and subsequently iterated to the locked configuration.

3. The plate of claim 2, wherein the securement direction is defined by a proximal direction that is opposite the distal direction.

4. The plate of claim 3, wherein the securement head is aligned with the retention wall when the securement head is in the locked configuration, and is out of alignment with the retention wall when the securement head is in the unlocked configuration.

5. A plate configured to secure to an intervertebral implant that extends in a distal direction from the plate, the plate comprising:
   a plate body having at least one bone fixation hole configured to receive a bone fixation element that is driven into a vertebral body, wherein the plate body defines a seat; and
   a securement member is configured to rotate in a first direction of rotation about an axis of rotation from an unlocked configuration to a locked configuration,
   wherein the securement member is configured to be driven to translate in a securement direction along the axis of rotation to a secured position until a retention wall of the intervertebral implant is captured between the seat and the securement member when the securement member is in the locked configuration,
   wherein the securement member comprises a securement shaft and a securement head, wherein the securement head is configured to be inserted into the implant when the securement member is in the unlocked configuration and subsequently iterated to the locked configuration, and wherein the securement head is oblong and is in a first orientation in the unlocked configuration, and a second orientation different than the first orientation in the locked configuration.

6. The plate of claim 5, wherein the securement head extends in opposite directions from the securement shaft.

7. The plate of claim 5, wherein the securement head extends in opposite directions from a terminal end of the securement shaft, such that the securement member is substantially T-shaped.

8. The plate of claim 5, wherein the first and second orientations are approximately 90 degrees offset to each other.

9. The plate of claim 2, wherein the securement member is configured to be driven to translate in the securement direction while the securement member is rotated in the first direction of rotation.

10. The plate of claim 9, further comprising an auxiliary shaft that is positionally fixed with respect to the plate body, wherein the auxiliary shaft interfaces with the securement shaft so as to drive the securement member to travel in the securement direction during rotation of the securement member.

11. The plate of claim 10, wherein the axis of rotation is oriented along a longitudinal direction, the securement member comprises a track that extends along the longitudinal direction as it extends circumferentially about the securement shaft, and the auxiliary shaft is coupled to the track and is positionally fixed with respect to the plate body.

12. The plate of claim 11, wherein the track comprises a recess that extends into the securement shaft, and the auxiliary shaft extends into the recess.

13. The plate of claim 1, wherein the actuator is configured to drive the securement member to travel in the securement direction only when the securement member is in the locked configuration.

14. The plate of claim 2, wherein the securement member rotates in the first direction of rotation with the actuator until the securement member is in the locked configuration, at which point further rotation of the actuator in the first direction of rotation is relative to the securement shaft.

15. The plate of claim 1, wherein the plate is configured to be secured to the intervertebral implant selectively prior to and after implantation of the implant into an intervertebral space.

16. The plate of claim 1, wherein the at least one bone fixation hole comprises a first bone fixation hole configured to receive a first bone fixation element that extends into a first vertebral body, and a second bone fixation hole configured to receive a second bone fixation element that extends into a second vertebral body, wherein an intervertebral space is disposed between the first and second vertebral bodies that is configured to receive the intervertebral implant.

17. The plate of claim 1, wherein at least one bone fixation hole is the only bone fixation hole of the plate, wherein the bone fixation hole is in a first position.

18. The plate of claim 1, further comprising a cam member that is rotatable from a first position that is spaced from a head of the bone fixation element, to a second position whereby the cam member interferes with the head so as to prevent back-out of the bone fixation element.

19. The plate of claim 18, wherein an inner surface of the cam member progressively moves toward the head of the bone fixation element as it rotates in a direction from the first position to the second position, and the inner surface of the cam member applies a retention force against the head of the bone fixation element when the cam member is in the second position.

*    *    *    *    *